(12) United States Patent
Kitagawa

(10) Patent No.: US 8,815,180 B2
(45) Date of Patent: Aug. 26, 2014

(54) SAMPLE PROCESSING APPARATUS

(75) Inventor: Nobuhiro Kitagawa, Akashi (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 0 days.

(21) Appl. No.: 13/194,059

(22) Filed: Jul. 29, 2011

(65) Prior Publication Data

US 2012/0028343 A1 Feb. 2, 2012

(30) Foreign Application Priority Data

Aug. 2, 2010 (JP) ................................. 2010-174024
Jun. 29, 2011 (JP) ................................. 2011-144085

(51) Int. Cl.
*G01N 1/02* (2006.01)
*G01N 35/00* (2006.01)
*G01N 35/10* (2006.01)
*G01N 35/04* (2006.01)

(52) U.S. Cl.
CPC ...... *G01N 35/00722* (2013.01); *G01N 35/1011* (2013.01); *G01N 2035/0493* (2013.01)
USPC ........ 422/509; 422/561; 422/68.1; 435/286.1

(58) Field of Classification Search
CPC .................. G01N 35/00722; G01N 35/00732; G01N 2035/1011; G01N 2035/0493
See application file for complete search history.

(56) References Cited

U.S. PATENT DOCUMENTS

| | | | |
|---|---|---|---|
| 6,495,104 B1 * | 12/2002 | Unno et al. | 422/68.1 |
| 2008/0050279 A1 * | 2/2008 | Fujita | 422/67 |
| 2008/0219886 A1 * | 9/2008 | Fukuju et al. | 422/63 |
| 2010/0159603 A1 | 6/2010 | Hamada et al. | |

FOREIGN PATENT DOCUMENTS

| | | | |
|---|---|---|---|
| CN | 101762713 A | | 6/2010 |
| GB | 1312656 | * | 4/1973 |
| JP | 05-036364 A | | 5/1993 |
| JP | 2001-264340 A | | 9/2001 |

* cited by examiner

*Primary Examiner* — P. Kathryn Wright
(74) *Attorney, Agent, or Firm* — Brinks Gilson & Lione

(57) ABSTRACT

There is provided a sample processing apparatus capable of detecting the push-up type sample container including a recess on the outer side of the bottom portion of the container and performing an appropriate sample processing while alleviating the load of the user with a simple configuration.

16 Claims, 21 Drawing Sheets

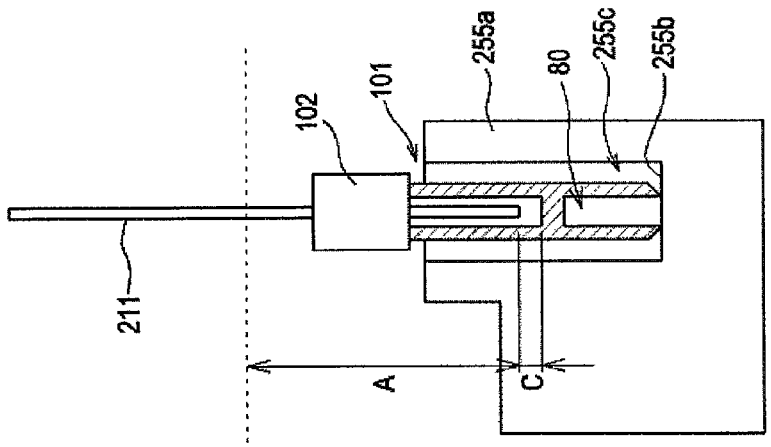
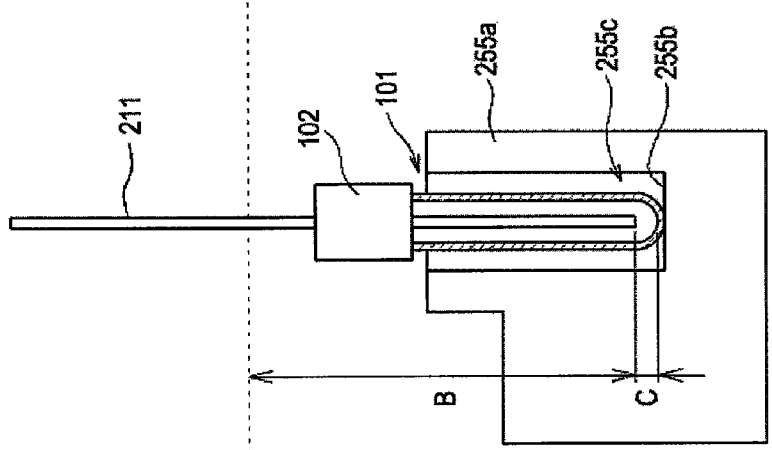
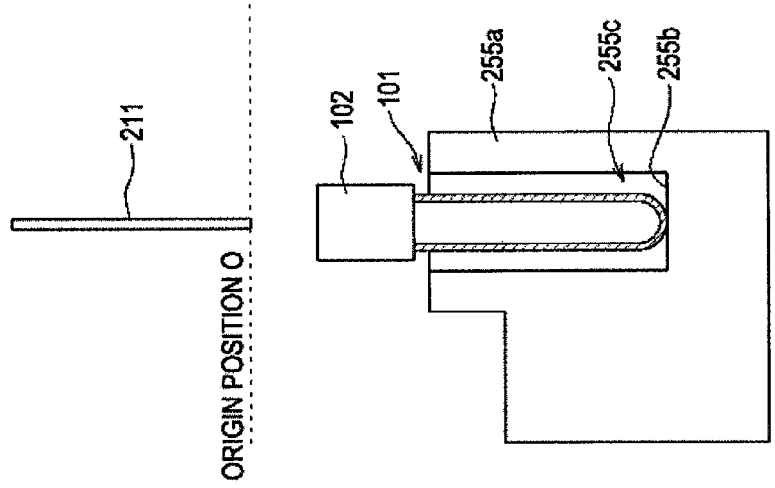

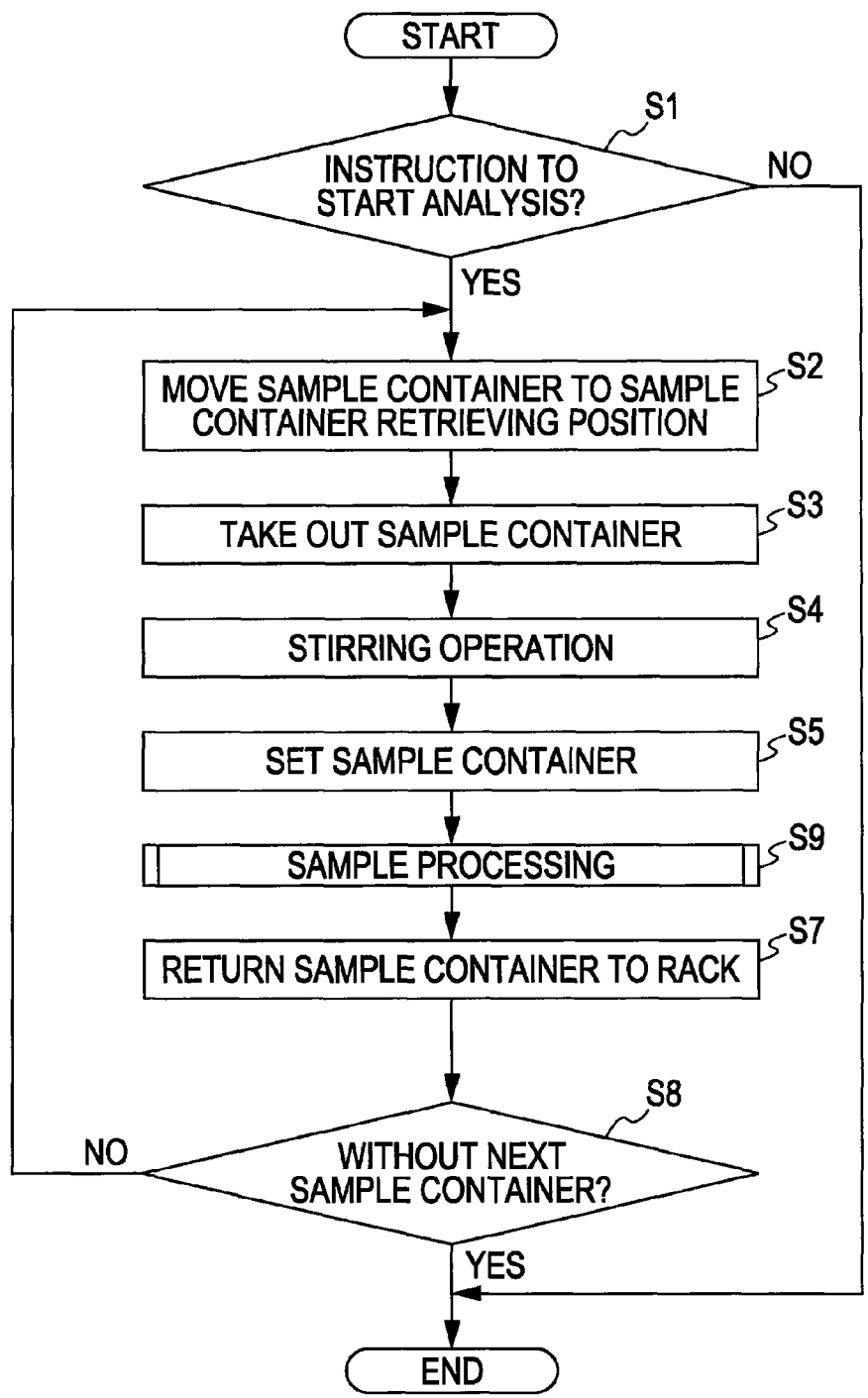

SAMPLE PROCESSING APPARATUS

RELATED APPLICATIONS

This application claims priority under 35 U.S.C. §119 to Japanese Patent Application Nos. 2010-174024 filed on Aug. 2, 2010 and 2011-144085 filed on Jun. 29, 2011, the entire contents of which are hereby incorporated by reference.

BACKGROUND OF THE INVENTION

1. Field of the Invention

The present invention relates to a sample processing apparatus. More specifically, the present invention relates to a sample processing apparatus for carrying out processes such as aspirating a sample in a sample container with an aspirating tube, analyzing the aspirated sample, and preparing the blood smear sample.

2. Description of the Related Art

A sample container in which the internal volume of the sample container is reduced by positioning the bottom on the inner side of the sample container to the upper side is conventionally known (see e.g., Japanese Laid-Open Utility Model Publication No. 5-36364). The sample container described in Japanese Laid-Open Utility Model Publication No. 5-36364 is a push-up bottom type in which the bottom portion on the inner side of the container is positioned on the upper side, and includes a recess on the outer side of the bottom portion of the container.

An analyzer for detecting the type of sample container and controlling the lowering amount of the aspirating tube so that the aspirating tube inserted into the container to aspirate the sample in the sample container does not touch the inner side of the bottom portion of the container and be damaged is also known (see e.g., Japanese Laid-Open Patent Publication No. 2001-264340). The analyzer described in Japanese Laid-Open Patent Publication No. 2001-264340 detects the type of sample container by causing the barcode reader to read the barcode, which contains information on the type of sample container, attached to the side surface of the sample container, and controls the lowering amount of the aspirating tube in correspondence with the detected type. Japanese Laid-Open Patent Publication No. 2001-264340 also describes that the analyzer may control the lowering amount of the aspirating tube in correspondence with the type of sample container by inputting information of the sample container with a keyboard, or the like.

If two types of sample containers, a push-up bottom type sample container including a recess on the outer side of the bottom portion of the container as in Japanese Laid-Open Utility Model Publication No. 5-36364 and a non-push-up type normal container not including a recess on the outer side of the bottom portion are used in the analyzer described in Japanese Laid-Open Patent Publication No. 2001-264340, the barcode containing information on the type of sample container is attached to the side surface of the sample container, the content is read by the barcode reader to detect which of the two types of sample containers the sample container is, and the lowering amount of the aspirating tube needs to be controlled in correspondence with the detected type. Furthermore, the lowering amount of the aspirating tube needs to be controlled in correspondence with the type of sample container if the information of the sample container is input by keyboard, or the like.

However, if the barcode is used for the detection of the type of sample container, the type of sample container may not be correctly read if the barcode is attached to an inappropriate position by mistake or the barcode is dirty. Furthermore, it is troublesome to input the type of sample container by keyboard, or the like each time.

In view of such situations, it is an object of the present invention to provide a sample processing apparatus capable of detecting the push-up type sample container including a recess on the outer side of the bottom portion of the container and performing an appropriate aspiration while alleviating the load of the user with a simple configuration.

SUMMARY OF THE INVENTION

The scope of the present invention is defined solely by the appended claims, and is not affected to any degree by the statements within this summary.

(1) In accordance with a first aspect of the present invention, a sample processing apparatus for processing a sample accommodated in a sample container comprising:

a holder on which a first type of sample container and a second type of sample container is to be set, wherein the first type of sample container includes a recess formed on an outer side of a lower portion, and the second type of sample container does not include the recess;

a sample processing unit for processing a sample accommodated in a sample container set in the holder;

a recess detector for detecting the recess of the sample container set in the holder; and a controller for controlling the sample processing unit to process the sample under a first sample processing condition if the recess is not detected by the recess detector, and to process the sample under a second sample processing condition different from the first sample processing condition if the recess is detected by the recess detector.

BRIEF DESCRIPTION OF THE DRAWINGS

FIGS. 12A, 12B and 12C are explanatory views showing the relationship of the lowering amount of the aspirating tube according to the sample container type;

FIG. 13 is a flowchart showing a flow of processes of the blood specimen processing method according to a second embodiment;

FIG. 21 is an illustrative view of the calculation processing result of the measurement data.

DETAILED DESCRIPTION OF THE PREFERRED EMBODIMENTS

The embodiments of the sample processing apparatus of the present invention will be described in detail below with reference to the accompanying drawings.

First Embodiment

Sample Processing Apparatus

First, an overall configuration of a blood specimen processing apparatus serving as an example of the sample processing apparatus of the present invention will be described.

Figure 1:
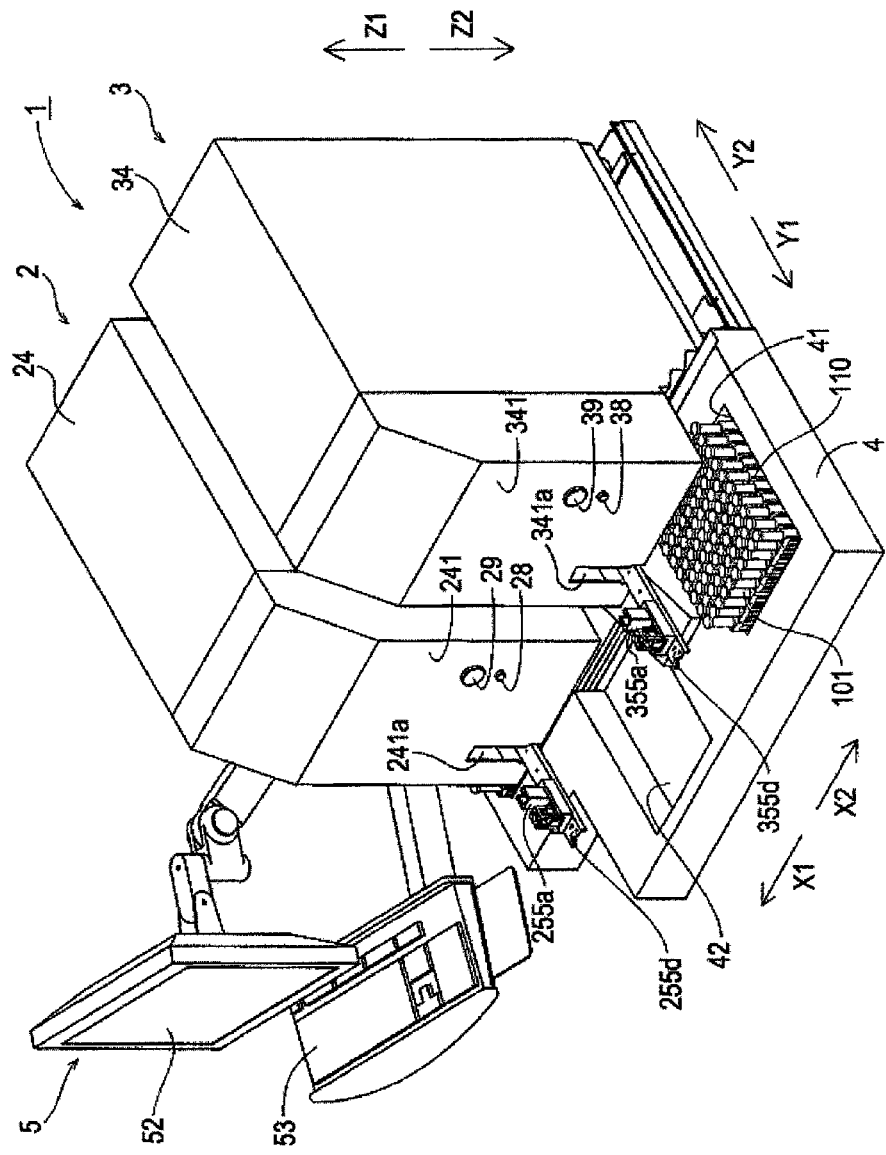
FIG. 1 is a perspective view showing an overall configuration of one embodiment of a sample processing apparatus of the present invention.

The blood specimen processing apparatus 1 shown in FIG. 1 is a blood cell counting apparatus for counting the blood cells in the blood specimen or the sample collected from the subject, and includes two measurement units, a first measurement unit 2 and a second measurement unit 3, a sample transporting device (sampler) 4 arranged on the front surface side (arrow Y1 direction side) of the first measurement unit 2 and the second measurement unit 3, and a control device 5 including a PC (personal computer) electrically connected to the first measurement unit 2, the second measurement unit 3, and the sample transporting device 4, as shown in the figure. The blood specimen processing apparatus 1 is connected to a host computer 6 (see FIG. 2) by the control device 5.

Figure 2:
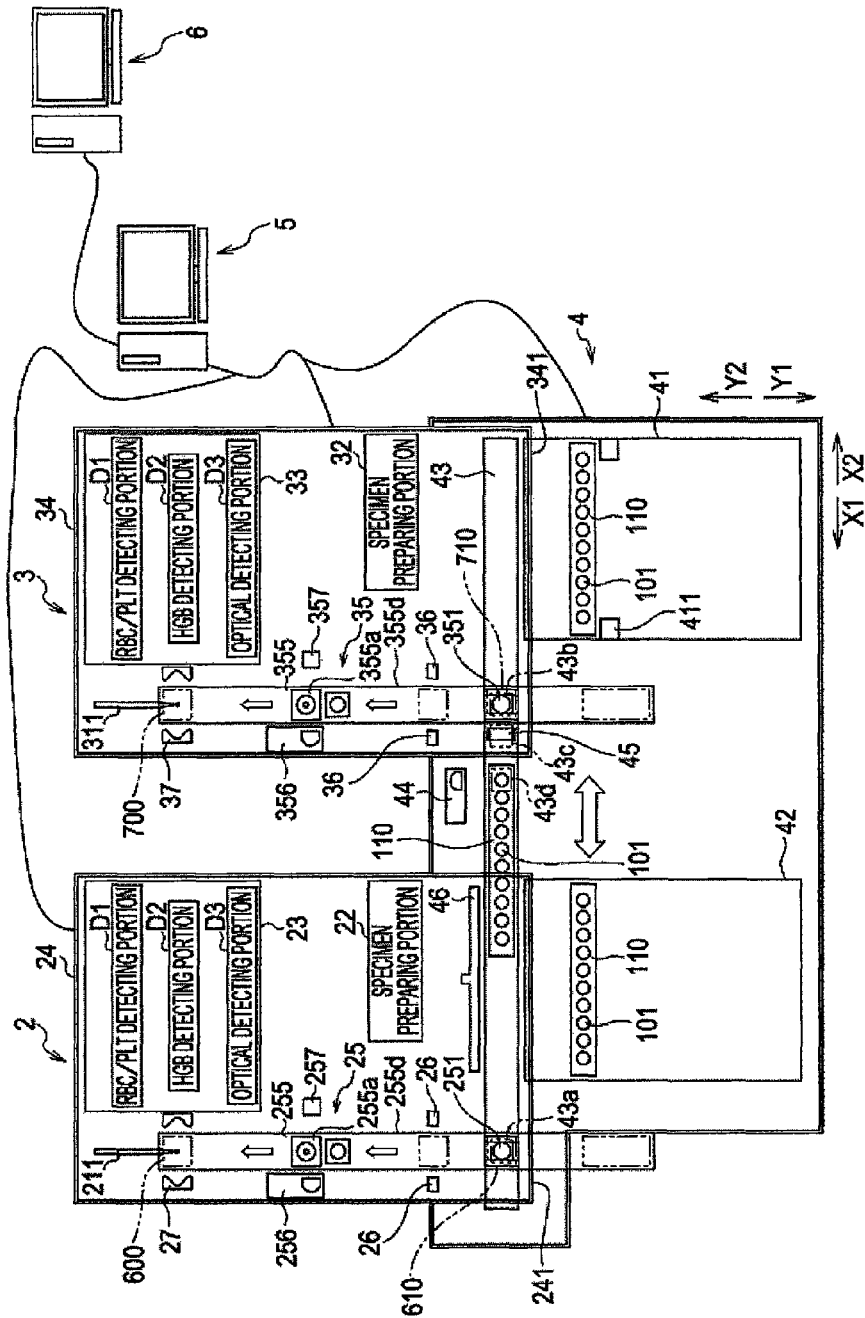
FIG. 2 is a schematic explanatory view showing a measurement unit and a sample transporting device of the sample processing apparatus shown in FIG. 1.

As shown in FIG. 1 to FIG. 2, the first measurement unit 2 and the second measurement unit 3 are substantially the same type of measurement units and are arranged adjacent to each other. Specifically, in the present embodiment, the second measurement unit 3 uses the same measurement principle as the first measurement unit 2 and measures the sample for the same measurement item. The second measurement unit 3 also measures for the measurement item not analyzed by the first measurement unit 2. As shown in FIG. 2, the first measurement unit 2 and the second measurement unit 3 each includes an aspirating tube 211 (311) for aspirating blood or a sample from a sample container 101, a specimen preparing portion 22, 32 for preparing a measurement specimen from the blood aspirated by the aspirating tube 211 (311), and a detecting portion 23, 33 for detecting the blood cells of the blood from the measurement specimen prepared by the specimen preparing portion 22, 32.

The first measurement unit 2 and the second measurement unit 3 also respectively includes a unit cover 24, 34 internally accommodating the specimen preparing portion 22, 32 and the like, a sample container transporting portion 25, 35 for retrieving the sample container 101 to inside the unit cover 24, 34 and transporting the sample container 101 to an aspirating position 600, 700 (see FIG. 2) by the aspirating tube 211 (311), a presence/absence detecting portion 26, 36 for detecting presence or absence of the sample container 101 transported inside by the sample container transporting portion 25, 35, and a chuck portion 27, 37 for fixing and holding the sample container 101 at the aspirating position 600, 700. As shown in FIG. 1, the outer side surface of the front surface 241, 341 of the unit cover 24, 34 each includes a sample set portion open/close button 28, 38, a priority sample measurement start button 29, 39, and an opening 241a, 341a through which a moving part 255d, 355d, to be described later, of the sample container transporting portion 25, 35 passes.

Figure 3:
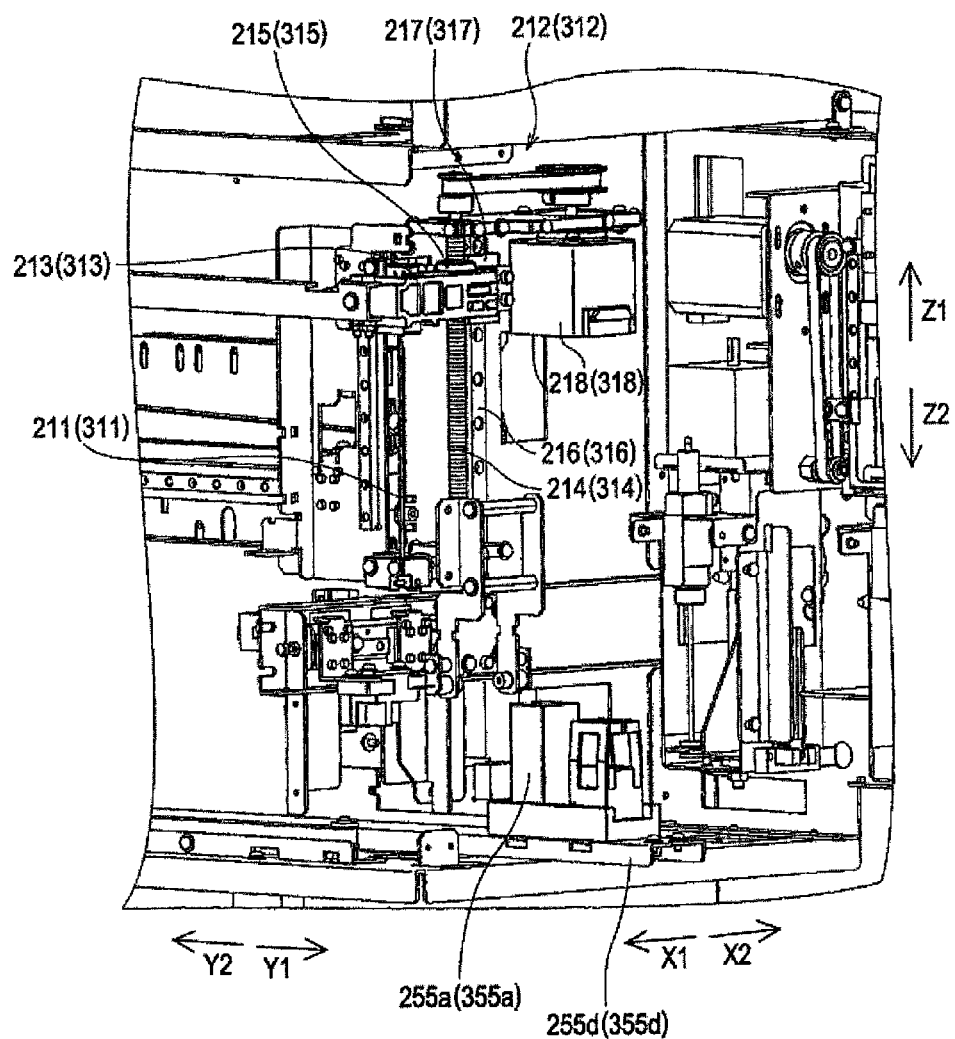
FIG. 3 is a perspective view showing the vicinity of the aspirating tube of the sample processing apparatus shown in FIG. 1.

FIG. 3 is a view showing a vicinity of the aspirating tube 211 (311). As shown in FIG. 3, the blood specimen processing apparatus 1 includes the aspirating tube 211 (311), and an aspirating tube moving portion 212 (312) or a drive portion for moving the aspirating tube 211 (311) in the up and down direction through the lid of the sample container 101. The aspirating tube 211 (311) is configured such that the distal end can pass through the lid of the sample container 101. The outer peripheral surface of the aspirating tube 211 (311) is formed with a groove extending in the longitudinal direction of the aspirating tube 211 (311), where the interior of the sample container 101 is opened to outside air through the groove when the aspirating tube 211 (311) is passed through the lid of the sample container 101. The aspirating tube moving portion 212 (312) has a function of moving the aspirating tube 211 (311) in the up and down direction (direction of arrows Z1 and Z2). The aspirating tube moving portion 212 (312) includes a horizontal arm 213 (313) for fixing and holding the aspirating tube 211 (311), a screw shaft 214 (314) for passing the horizontal arm 213 (313) in the up and down direction (direction of arrows Z1 and Z2), and a nut 215 (315) for screwing the screw shaft 214 (314).

Furthermore, the aspirating tube moving portion 212 (312) includes a slide rail 216 (316) arranged parallel (direction of arrows Z1 and Z2) to the screw shaft 214 (314), a slidably moving member 217 (317) slidably attached to the slide rail 216 (316), and a stepping motor 218 (318). The horizontal arm 213 (313) is fixed to the nut 215 (315) and the slidably moving member 217 (317).

A detection unit 23 (33) is configured by an RBC/PLT detecting portion D1 used for the RBC measurement (measurement of number of red blood cells) and the PLT measurement (measurement of number of blood platelets), an HGB detecting portion D2 used for the HGB measurement (measurement of hemoglobin amount in blood), and an optical detecting portion D3 used for the WBC measurement (measurement of number of white blood cells), the DIFF measurement (classification of white blood cells), the NRBC measurement, and the RET measurement. The RBC/PLT detecting portion D1 is configured to carry out the RBC detection (detection of red blood cells) and the PLT detection (detection of blood platelets) through the sheath flow DC detection method, and the HGB detecting portion D2 is configured to carry out the HGB detection (detection of hemoglobin in blood) through the SLS-hemoglobin method. The optical detecting portion D3 is configured to carry out the WBC detection (detection of white blood cells) through the flow cytometry method using the semiconductor laser. Specifically, the optical detecting portion D3 detects the intensity of the forward scattered light, the intensity of the lateral scattered light, and the intensity of the lateral fluorescence emitted from the blood cells in the sheath flow cell irradiated with light as characteristic parameters of the blood cells by the flow cytometry method using the semiconductor laser. The characteristic parameters of the detected blood cells are used in the WBC measurement, the DIFF measurement, and the like. The WBC measurement is the measurement for counting the white blood cells and calculating the concentration of the white blood cells in the specimen, and the DIFF measurement is the measurement for classifying the white blood cells to the lymphocytes, the basocytes, the acidocytes, the neutrophil, and the monocytes, and counting the respective concentration in the specimen.

The detection results obtained by the detecting portion 23 (33) are transmitted to the control device 5 as measurement data (measurement result) of the sample. The measurement data is data that becomes the basis of the final analysis result (number of red blood cells, number of blood platelets, hemoglobin amount, number of white blood cells, etc.) to be provided to the user.

Figure 4:
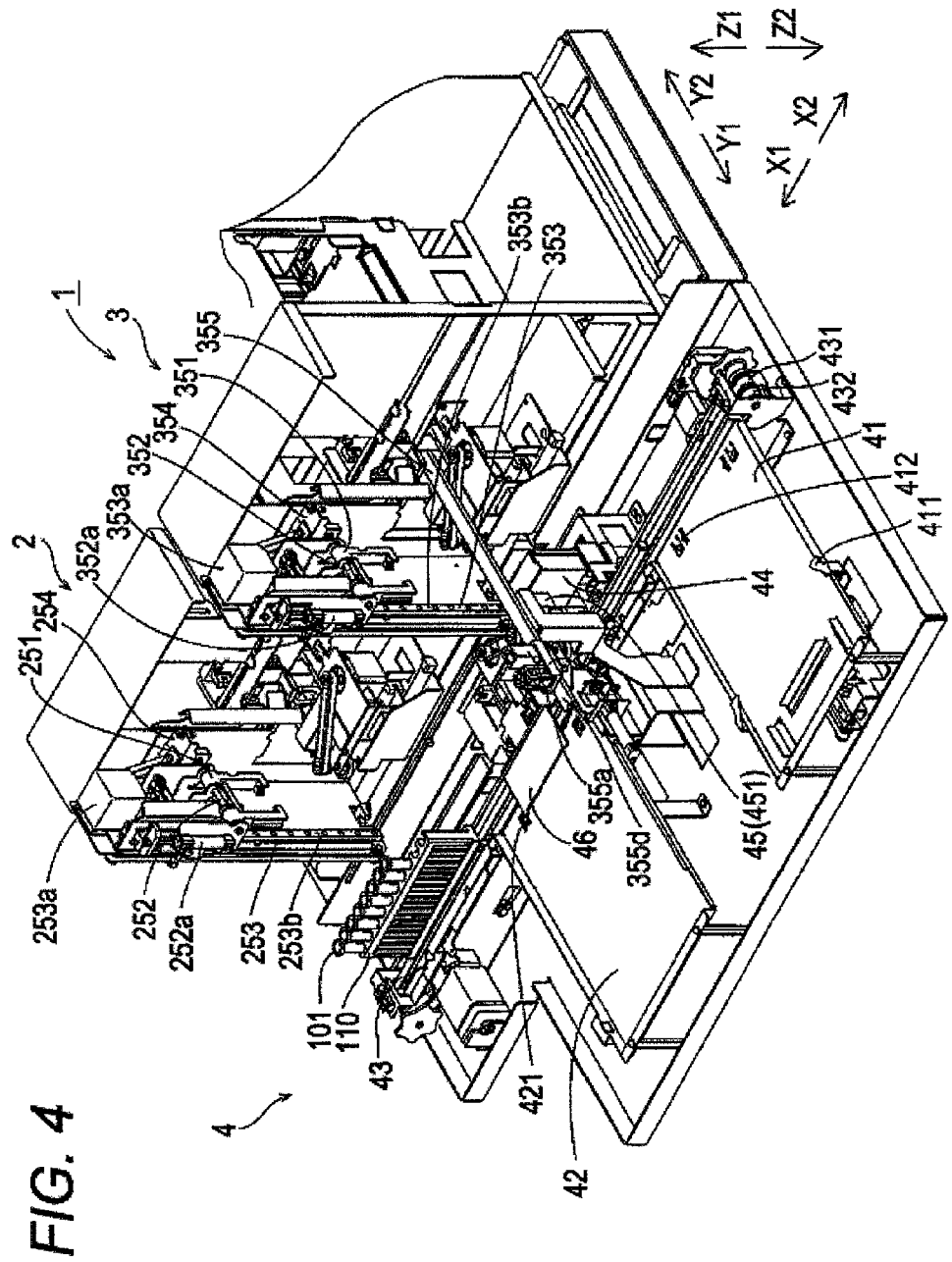
FIG. 4 is a perspective view showing the measurement unit and the sample transporting device of the sample processing apparatus shown in FIG. 1.

As shown in FIG. 4, the sample container transporting portion 25 (35) (see FIG. 2) includes a hand 251 (351) or a container holder for gripping the sample container 101, an open/close part 252 (352) for opening and closing the hand 251 (351), an up and down moving part 253 (353) for linearly moving the hand 251 (351) in the up and down direction (direction of arrows Z1 and Z2), and a stirring motor 254 (354) for moving (turning) the hand 251 (351) in a pendulum form between an upright state and a fallen state. The stirring motor 254 (354) is configured to move (turn) the hand 251 (351) in a pendulum form between the upright state and the fallen state by the power from the stepping motor. As shown in FIG. 2, the sample container transporting portion 25 (35) also includes a sample container transfer part 255 (355) for substantially horizontally moving the sample container 101 in the direction of the arrows Y1 and Y2, and a barcode reader 256 (356). In the present embodiment, a container detecting part 257 (357) with a pair of fixed rollers 61, a holder 62 having the fixed roller 61 rotatably attached at the distal end, and a sensor 63 is arranged. The container detecting part 257 (357) is arranged in the vicinity of the barcode reader 256 (356) (see FIG. 2). A sample container rotation roller 60 for rotating the sample container 101 set in the sample setting part 255a is arranged at the position facing the pair of fixed rollers 61 so that the barcode attached to the sample container 101 can be read by the barcode reader 256 (356).

The hand 251 (351) is arranged on the upper side of the transport path of the rack 110 transported by the sample transporting device 4. The hand 251 (351) is configured to be moved to the lower side (direction of arrow Z2) and then opened/closed by the open/close part 252, 352 to grip the sample container 101 accommodated in the rack 110 when the sample container 101 is transported to the first retrieving position 43a and the second retrieving position 43b (see FIG. 3) by the sample transporting device 4.

The hand 251 (351) is also configured to take out the sample container 101 from the rack 110 by moving the gripped sample container 101 to the upper side (direction of arrow Z1), and then moved in a pendulum form (e.g., reciprocate ten times), by the stirring motor 254 (354). The hand 251 (351) then can stir the blood in the sample container 101 being gripped. After the stirring is finished, the hand 251 (351) is moved to the lower side (direction of arrow Z2) to open the gripping of the sample container 101 by the open/close part 252 (352). Specifically, the hand 251 (351) is configured to set the sample container 101 in the sample setting part 255a (355a) moved to the sample setting position 610 (710) (see FIG. 2) by the sample container transfer part 255 (355). As shown in FIG. 2, the first retrieving position (sample container retrieving position) 43a and the sample setting position (sample container setting position) 610 are arranged to overlap, and the second retrieving position (sample container retrieving position) 43b and the sample setting position (sample container setting position) 710 are arranged to overlap when viewed in plan view. As shown in FIG. 3, the sample setting part 255a (355a) includes a recess detecting section 70 in the present embodiment. As shown in FIG. 10, the recess detecting section 70 includes an arm 71 or an elongate body arranged at the bottom of the sample setting part 255a and a sensor 72 arranged in the vicinity of one end of the arm 71. The arm 71 is supported in a freely rotating manner at the shaft 73 arranged at the bottom of the sample setting part 255a.

The open/close part 252 (352) is configured to open/close the hand 251 (351) to grip the sample container 101 by the power of the air cylinder 252a (352a).

The up and down moving part 253 (353) is configured to move the hand 251 (351) in the up and down direction (direction of arrows Z1 and Z2) along the rail 253b (353b) by the power of the stepping motor 253a (353a).

The chuck portion 27 (37) is configured to fix and hold the sample container 101 transferred to the aspirating position 600 (700).

The pre-analysis rack holding portion 41 includes a rack sending part 411, and is configured to push out the rack 110 held by the pre-analysis rack holding portion 41 onto the rack transporting portion 43 one at a time by moving the rack sending part 411 in the direction of the arrow Y2. The rack sending part 411 is configured to be driven by a stepping motor (not shown) arranged on the lower side of the pre-analysis rack holding portion 41. The pre-analysis rack holding portion 41 includes a regulating part 412 (see FIG. 4) in the vicinity of the rack transporting portion 43, and is configured to regulate the movement of the rack 110 so that the rack 110 pushed out onto the rack transporting portion 43 once cannot return to the pre-analysis rack holding portion 41.

A post-analysis rack holding portion 42 includes a regulating part 421 (see FIG. 4) in the vicinity of the rack transporting portion 43, and is configured to regulate the movement of the rack 110 so that the rack 110 moved into the post-analysis rack holding portion 42 once cannot return to the rack transporting portion 43 side.

As shown in FIG. 2, the rack transporting portion 43 is configured to transport the rack 110 to transfer the sample container 101 held in the rack 110 to the first retrieving position 43a for providing the sample to the first measurement unit 2 and the second retrieving position 43b for providing the sample to the second measurement unit 3. Furthermore, the rack transporting portion 43 is configured to transport the rack 110 to transfer the sample container 101 to the sample presence/absence checking position 43c for the presence/absence detection sensor 45 to check the presence/absence of the sample container 100 accommodating the sample and the reading position 43d for the barcode reading portion 44 to read the barcode of the sample container 101 accommodating the sample.

As shown in FIG. 4, the rack transporting portion 43 includes two belts, a first belt 431 and a second belt 432, that can move independent from each other.

The presence/absence detection sensor 45 is a contact type sensor, and includes a curtain shaped contact strip 451 (see FIG. 4), a light emitting element (not shown) for emitting light and a light receiving element (not shown). The presence/absence detection sensor 45 is configured such that the contact piece 451 bends when brought into contact with a detecting object to be detected, and as a result, the light emitted from the light emitting element is reflected by the contact piece 451 thus entering into the light receiving element. The contact piece 451 is thus bent by the sample container 101 when the sample container 101 to be detected accommodated in the rack 110 passes the lower side of the presence/absence detection sensor 45, whereby the presence of the sample container 101 can be detected.

The rack sending portion 46 is arranged to face the post-analysis rack holding portion 42 with the rack transporting portion 43 in between, and is configured to horizontally move in the direction of the arrow Y1. Thus, when the rack 110 is transported to between the post-analysis rack holding portion 42 and the rack sending portion 46, the rack sending portion 46 is moved towards the post-analysis rack holding portion 42 thus pushing the rack 110 and moving into the post-analysis rack holding portion 42.

Figure 5:
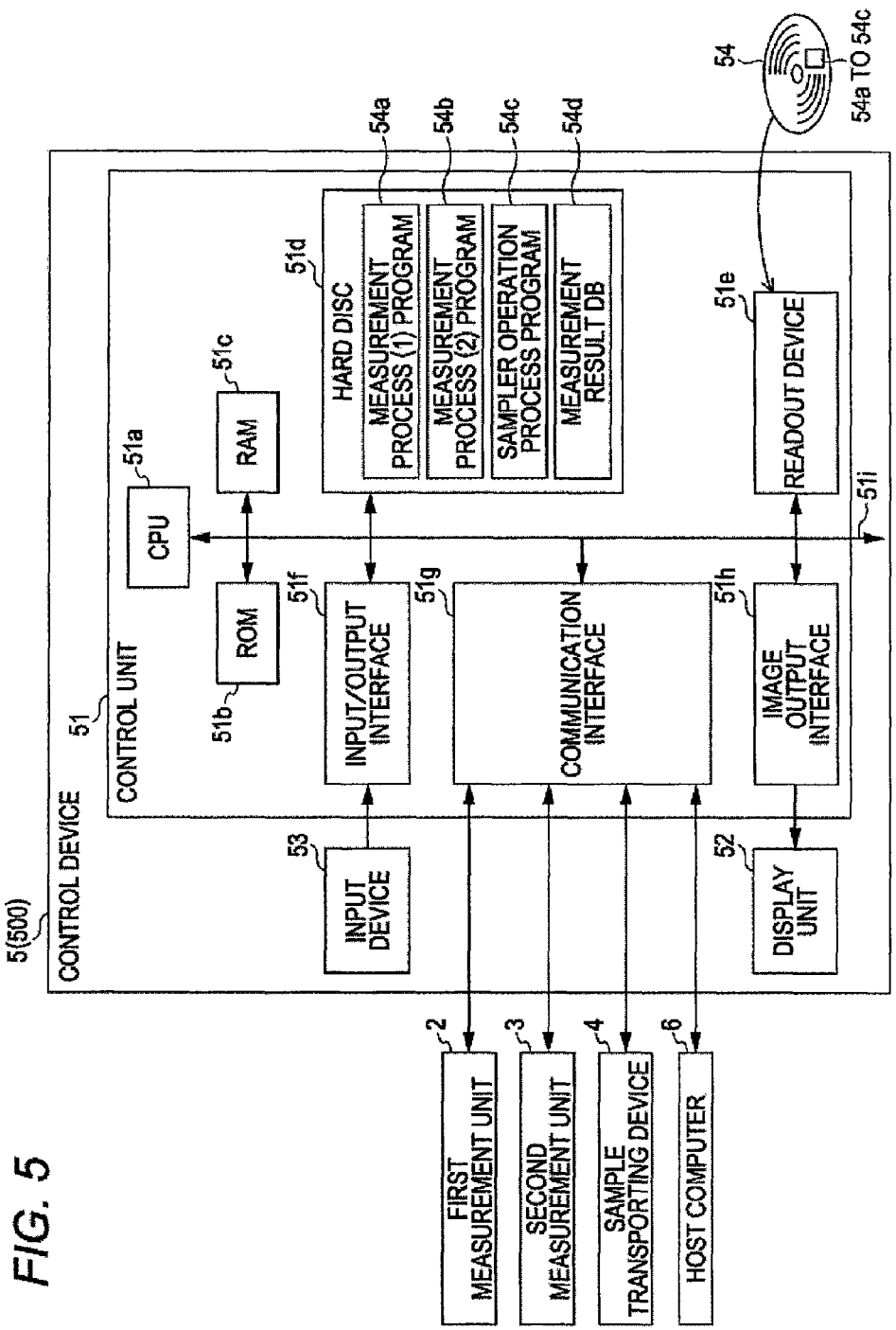
FIG. 5 is a block diagram describing a control device of the sample processing apparatus shown in FIG. 1.

As shown in FIGS. 1 to 2 and FIG. 5, the control device 5 includes a personal computer (PC) or the like, and includes a control unit 51 (see FIG. 5) including a CPU, a ROM, a RAM or the like, a display unit 52, and an input device 53. The display unit 52 is arranged to display the analysis result obtained by analyzing the data of the digital signal transmitted from the first measurement unit 2 and the second measurement unit 3.

As shown in FIG. 5, the control device 5 is configured by a computer 500 mainly configured by the control unit 51, the display 52, and the input device 53. The control unit 51 is mainly configured by a CPU 51a, a ROM 51b, a RAM 51c, a hard disc 51d, a read-out device 51e, an input/output interface 51f, a communication interface 51g, and an image output interface 51h. The CPU 51a, the ROM 51b, the RAM 51c, the hard disc 51d, the read-out device 51e, the input/output interface 51f, the communication interface 51g, and the image output interface 51h are connected by a bus 51i.

The CPU 51a is capable of executing a computer program stored in the ROM 51b and a computer program loaded in the RAM 51c. The computer 500 serves as the control device 5 when the CPU 51a executes the application programs 54a, 54b and 54c, as hereinafter described.

The ROM 51b is configured by mask ROM, PROM, EPROM, EEPROM, and the like, and is recorded with computer programs to be executed by the CPU 51a, data used for the same, and the like.

The RAM 51c is configured by SRAM, DRAM, and the like. The RAM 51c is used to read out the computer programs recorded on the ROM 51b and the hard disc 51d. The RAM 51c is used as a work region of the CPU 51a when executing the computer programs.

The hard disc 51d is installed with various computer programs to be executed by the CPU 51a such as operating system and application program, as well as data used in executing the computer program. The measurement process (1) program 54a for the first measurement unit 2, the measurement process (2) program 54b for the second measurement unit 3, and the sampler operation process program 54c for the sample transporting device 4 are also installed in the hard disc 51d. When the CPU 51a executes the application programs 54a to 54c, the operation of each portion of the first measurement unit 2, the second measurement unit 3 and the sample transporting device 4 is controlled. The hard disc 51d is also installed with the measurement result database 54d. The hard disc 51d is further stored with the lowering amount of the aspirating tube when aspirating the sample from the sample container by means of the aspirating tube. Specifically, the amount the aspirating tube is lowered from the origin position O to position at the aspirating position of a predetermined height is stored in correspondence with the type of sample container. FIG. 12 is an explanatory view showing the relationship of the lowering amount of the aspirating tube according to the sample container type. In FIG. 12, the recess detecting section 70 arranged in the sample setting part 255a is omitted. In the present embodiment, the lowering amount A is stored as the lowering amount of the aspirating tube for aspirating the sample from the sample container with the recess, and the lowering amount B greater than the lowering amount A is stored as the lowering amount of the aspirating tube for aspirating the sample from the sample container without the recess. Therefore, the aspirating position of when aspirating the sample from the sample container with the recess is the high position compared to the aspirating position of when aspirating the sample from the sample container without the recess. The lowering amount A is set at a position on the upper side from the inner side of the bottom portion of the container by a distance C so that the aspirating tube inserted into the sample container with the recess does not get damaged by contacting the inner side of the bottom portion of the container and can aspirate the sample. The lowering amount B is set at a position on the upper side from the inner side of the bottom portion of the container by a distance C so that the aspirating tube inserted into the sample container without the recess does not get damaged by contacting the inner side of the bottom portion of the container and can aspirate the sample. The distance C is preferably as small as possible.

The read-out device 51e is configured by flexible disc drive, CD-ROM drive, DVD-ROM drive, and the like, and is able to read out computer programs and data recorded on a portable recording medium 54. The application programs 54a to 54c are stored in the portable recording medium 54, where the computer 500 reads out the application programs 54a to 54c from the portable recording medium 54, and installs the application programs 54a to 54c to the hard disc 51d.

The application programs 54a to 54c are not only provided by the portable recording medium 54, and may be provided through telecommunication line (wired or wireless) from external devices communicatably connected with the computer 500 through the telecommunication line. For instance, the application programs 54a to 54c may be stored in the hard disc of the server computer on the Internet, so that the computer 500 can access the server computer to download the application programs 54a to 54c and install the application programs 54a to 54c to the hard disc 51d.

Operating system providing graphical user interface environment such as Windows (registered trademark) manufactured and sold by US Microsoft Co. is installed in the hard disc 51d. In the following description, the application programs 54a to 54c are assumed to operate on the operating system.

The input/output interface 51f is configured by serial interface such as USB, IEEE1394, RS-232C; parallel interface such as SCSI, IDE, IEEE1284; analog interface such as D/A converter, A/D converter, and the like. The input/output interface 51f is connected to the input device 53, so that the users can use the input device 53 to input data into the computer 500.

The communication interface 51g is, for example, Ethernet (registered trademark) interface. The computer 500 transmits and receives data with the first measurement unit 2, the second measurement unit 3, the sample transporting device 4, and the host computer 6 using a predetermined communication protocol by means of the communication interface 51g.

The image output interface 51h is connected to the display unit 52 configured by LCD, CRT, or the like, and is configured to output a video signal corresponding to the image data provided from the CPU 51a to the display unit 52. The display unit 52 displays the image (screen) according to the input video signal.

According to the configuration described above, the control unit 51 is configured to analyze the components to be analyzed using the measurement results transmitted from the first measurement unit 2 and the second measurement unit 3, and acquire the analysis result (number of red blood cells, number of blood platelets, hemoglobin amount, number of white blood cells, etc.).

[Blood Specimen Processing Method]

Figure 6:
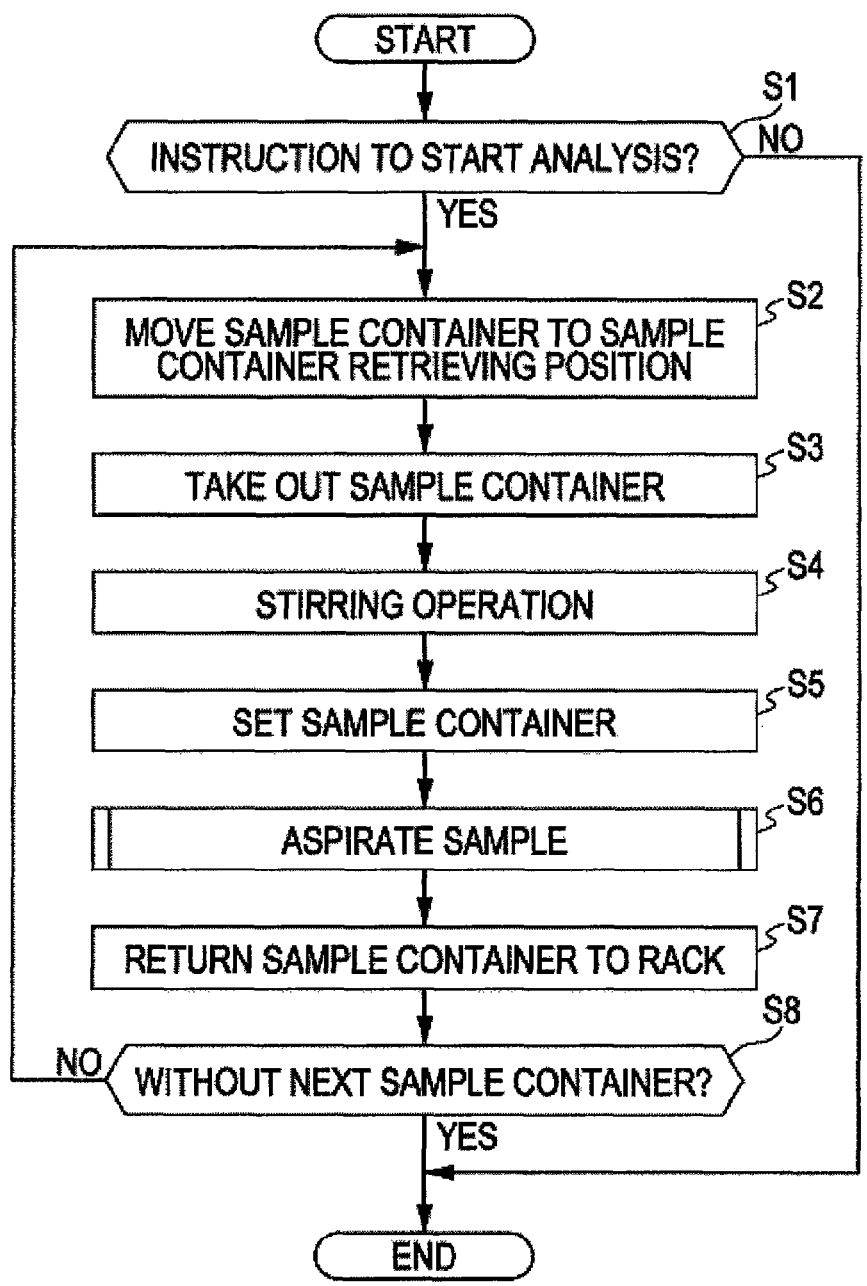
FIG. 6 is a flowchart showing flow of processes of the blood specimen processing method.
Figure 7:
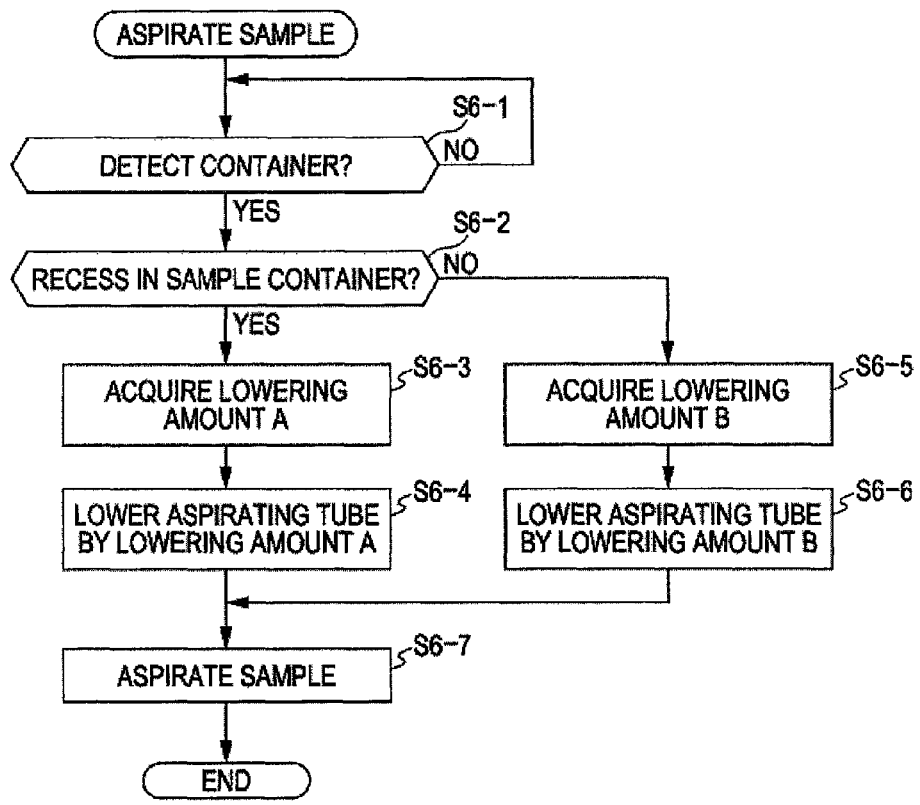
FIG. 7 is a flowchart showing flow of the aspirating operation of the blood specimen.

One example of the blood specimen processing method using the blood specimen processing apparatus 1 described above will be described centering on the aspirating operation, which is a characteristic operation, using FIGS. 6 and 7. In the first measurement unit 2 and the second measurement unit 3, analysis including stirring and aspiration of the sample is carried out with operations similar to each other, and hence the blood specimen processing method by the first measurement unit 2 will be described below and the description of the blood specimen processing method by the second measurement unit 3 will be omitted.

First, the rack 110 arranged with the sample container 101 with lid in which the blood specimen (sample) to be analyzed is accommodated is set on the sample transporting device 4 by the user. The CPU 51a of the control device 5 then determines that the instruction to start analysis is made when the start button is pushed in step S1 (Yes), controls the transportation of the rack 110 by the sample transporting device 4, and positions the sample container 101 at the first retrieving position (sample container retrieving position) 43a (step S2).

The CPU 51a then takes out the sample container 101 from the rack 110 using the hand 251 (step S3). Specifically, the CPU 51a drives the up and down drive part 253, so that the hand 251 is lowered from the upper side in an open state and stopped at the sample container holding position of holding the sample container 101.

The CPU 51a then drives the open/close part 252 to close the hand 251 and hold the sample container 101. The CPU 51a again drives the up and down drive part 253, so that the hand 251 is raised while holding the sample container 101, the sample container 101 is taken out from the rack 110, and the hand 251 is stopped at a predetermined position. In this state, the sample container 101 is in an upright state in which the axis in the longitudinal direction lies along substantially the perpendicular direction.

The CPU 51a then performs a falling and stirring operation of the sample container 101 by driving the stirring motor 254 (step S4). In the stirring step, the hand 251 holding the sample container 101 performs a forward and reverse rotation movement to stir the blood specimen accommodated in the sample container 101. The hand 251 carries out a falling and stirring operation including a first rotation step of rotating until reaching the fallen state in which the bottom portion of the sample container 101 is positioned on the upper side than the sealing lid 102 (see FIG. 10) of the sample container 101, and a second rotation step of reverse rotating until the sample container 101 returns to the upright state from the fallen state, for a predetermined number of times such as about ten times.

The rack 110 evacuates from the sample container retrieving position 43a during the stirring operation of the sample container 101, and then the sample setting part 255a moves forward up to a predetermined position on the lower side of the hand 251 by the drive of the sample container transporting portion 255.

After the end of stirring, the CPU 51a lowers the hand 251 and opens the hand 251 so that the sample container 101 held by the hand 251 is set in the sample setting part 255a (step S5).

The hand 251 is then raised, and the sample setting part 255a is drawn into the apparatus by the drive of the sample container transporting portion 255 and stopped right next to the barcode reader 256.

The CPU 51a then carries out the barcode reading of the sample container 101 and the aspirating operation of the sample from the sample container 101 (step S6). Specifically, the reading of the barcode attached to the sample container 101 and the detection of presence or absence of the sample container are carried out by the barcode reader 256 according to the control of the CPU 51a, and thereafter, the sample setting part 255a is positioned at the aspirating position 600, the aspirating tube 211 is driven and lowered by the aspirating tube driving portion 212 from the upper side while being held by the chuck portion 27 so that the sample container 101 does not move 101, and then passed through the sealing lid 102 of the sample container 101 and stopped at a predetermined position.

After the aspirating tube 211 is stopped at the predetermined position in the sample container 101, a predetermined amount of blood specimen is aspirated by the aspirating tube 211.

<Aspirating Operation>

The barcode reading operation and the aspirating operation in step S6, which are characteristic operations of the present invention, will now be described in detail with reference to FIG. 7.

Figure 8A:
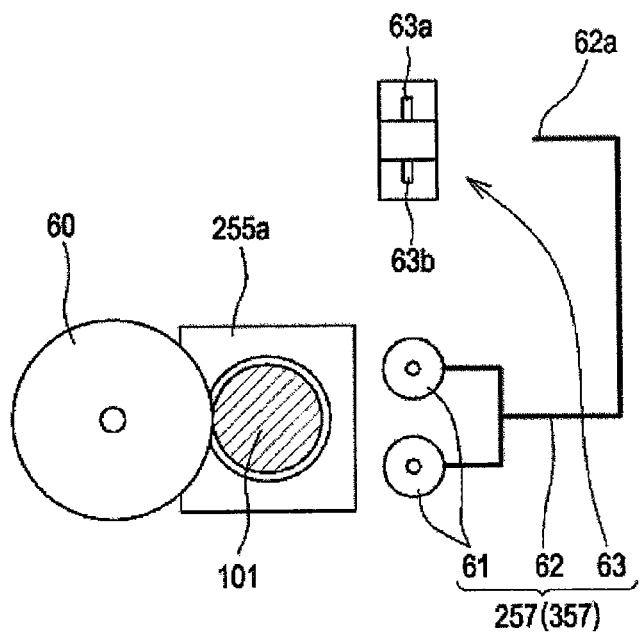
FIGS. 8A and 8B are operation explanatory views of the container detecting part when the sample container exists in the sample setting part.

First, in step S6-1, the detection of presence or absence of the sample container 101 in the sample setting part 255a drawn to right next to the barcode reader 256 in the apparatus by the sample container transporting portion 255 and the reading of the barcode attached to the sample container 101 are carried out. Specifically, as shown in FIGS. 8 and 9, the presence or absence of the sample container 101 is detected by the container detecting part 257 including a roller 60 for sample container rotation, a pair of fixed rollers 61, and a sensor 63. FIG. 8 is an operation explanatory view of the container detecting part 257 when the sample container 101 exists in the sample setting part 255a, and FIG. 9 is an operation explanatory view of the container detecting part 257 when the sample container 101 does not exist in the sample setting part 255a. In FIGS. 8 and 9 A shows a case in which the fixed roller 61 is at the backward moving position, and B shows a case in which the fixed roller 61 is at the forward moving position.

The roller 60 for sample container rotation is arranged so that the outer circumferential surface of the roller 60 can contact the outer peripheral surface of the sample container 101 when the sample container 101 is set in the sample setting part 255a right next to the barcode reader 256. The pair of fixed rollers 61 are arranged on the opposite side of the roller 60 with the sample setting part 255a in between. The fixed roller 61 is attached in a freely rotating manner at the distal end of a holder 62 having a forked distal end, where the holder 62 is configured to move forward and backward with respect to the roller 60 by a drive mechanism (not shown). In other words, it can be moved along a direction of moving closer to the roller 60 and a direction of moving away from the roller 60.

The sensor 63 capable of detecting the movement of the end 62*a* of the holder 62 is arranged in the vicinity of the fixed roller 60. The sensor 63 according to the present embodiment includes a light receiving part 63*a* and a light receiving part 63*b* and optically detects the existence of the end 62*a* of the holder 62, but a known sensor based on other principles such as magnetic type or contact type may be appropriately used for the sensor 63.

Figure 8B:
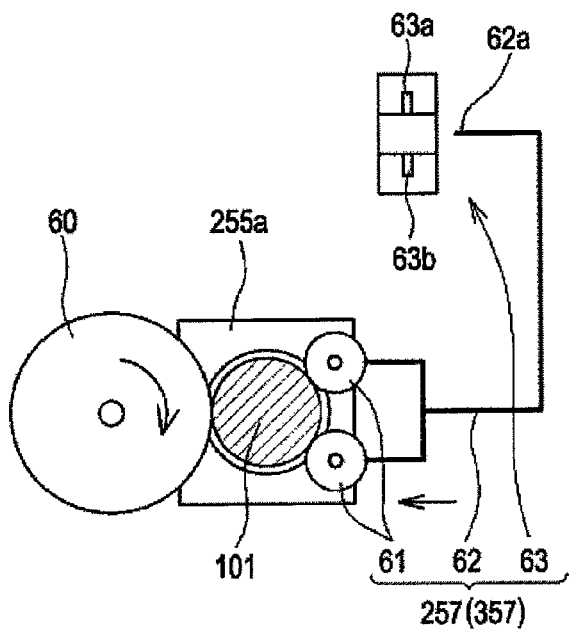
Figure 9A:
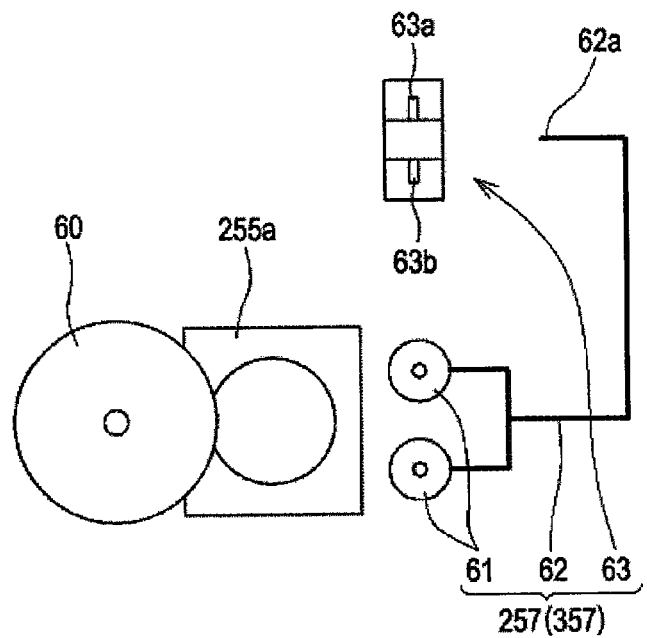
FIGS. 9A and 9B are operation explanatory views of the container detecting part when the sample container does not exist in the sample setting part.

If the sample container 101 is set in the sample setting part 255*a*, the pair of fixed rollers 63 moving toward the roller 60 stop when contacting the outer peripheral surface of the sample container 101, as shown in FIG. 8B. In this case, the end 62*a* of the holder 62 does not reach the space between the light emitting part 63*a* and the light receiving part 63*b* of the sensor 63, and thus the light emitted from the light emitting part 63*a* reaches the light receiving part 63*b* without being inhibited (sensor OFF). Determination is thus made that the sample container 101 is set in the sample setting part 255*a*.

Figure 9B:
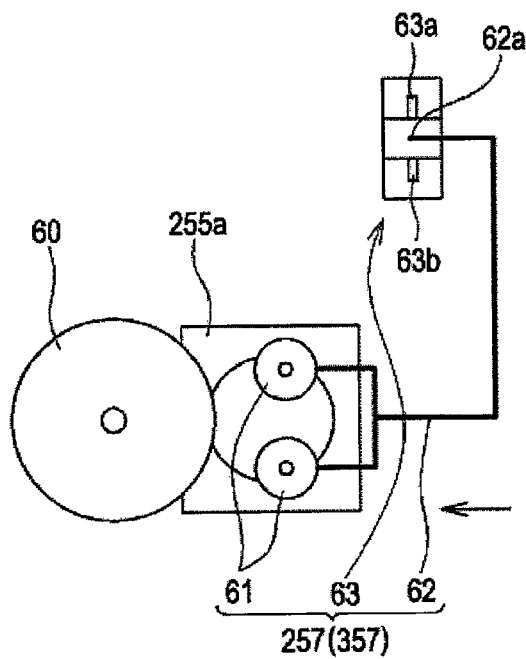

If the sample container 101 is not set in the sample setting part 255*a*, the pair of fixed rollers 63 moving toward the roller 60 stop at a predetermined stop position set further on the roller 60 side than the contact scheduled position without contacting the outer peripheral surface of the sample container 101, as shown in FIG. 9B. In this case, the end 62*a* of the holder 62 reaches the space between the light emitting part 63*a* and the light receiving part 63*b* of the sensor 63, and thus the light emitted from the light emitting part 63*a* is inhibited by the end 62*a* so that the amount of light reaching the light receiving part 63*b* becomes smaller than or equal to a threshold value (sensor ON). Determination is thus made that the sample container 101 is not set in the sample setting part 255*a*.

If determined that the sample container 101 is set in the sample setting part 255*a* in step S6-1 (Yes) the sample setting part 255*a* is positioned at the aspirating position 600, and the CPU 51*a* makes a determination on whether or not a recess 80 exists at the lower part of the sample container 101 set in the sample setting part 255*a* in step S6-2, In other words, whether or not the sample container 101 set in the sample setting part 255*a* is a push-up bottom type sample container with the recess 80 at the lower part or a normal sample container without the recess 80 at the lower part is determined. This determination may be made using the recess detecting section 70.

Figure 10A:
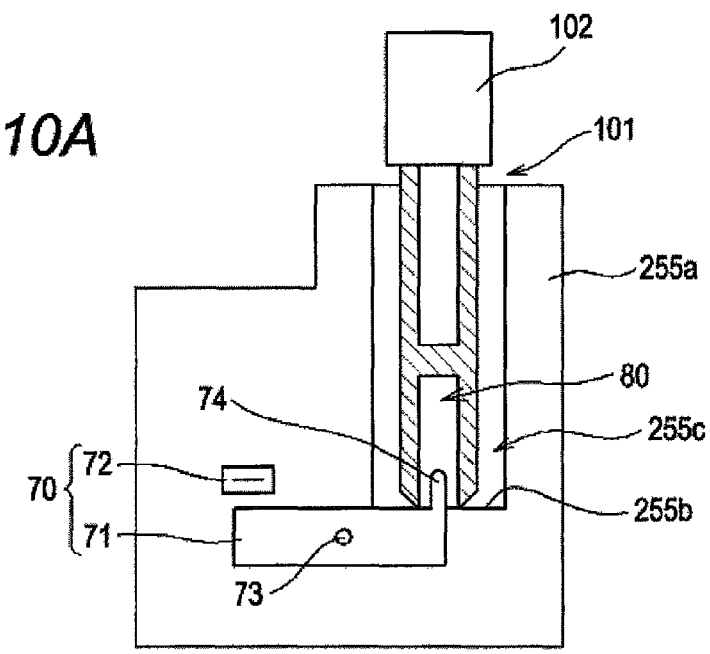
FIGS. 10A and 10B are explanatory views of a contact type recess detecting section.
Figure 10B:
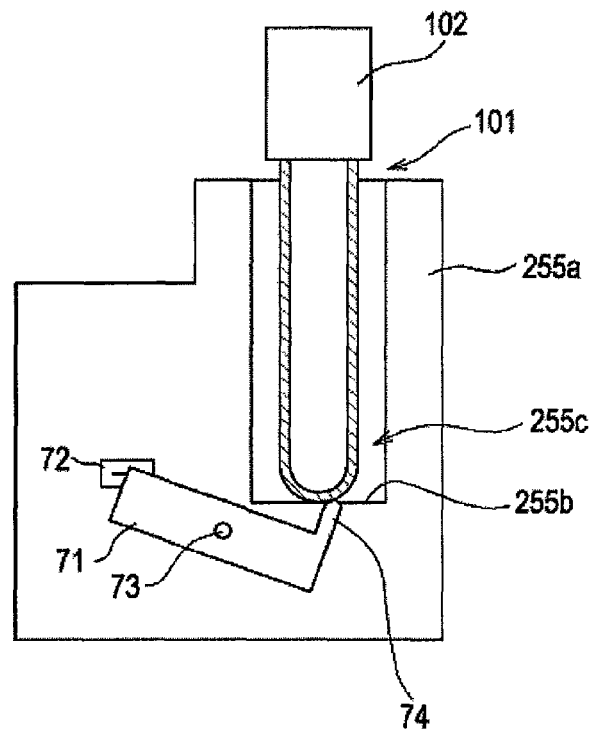

FIG. 10 is an explanatory view of the recess detecting section 70, which recess detecting section 70 is a contact type detecting section for detecting the recess 80 arranged on the outer side of the bottom portion of the sample container 101 by direct contact with the surface of the sample container 101. FIG. 10A shows a case in which the sample container 101 with the recess 80 is set in the sample setting part 255*a*, and FIG. 10B shows a case in which the sample container 101 without the recess 80 is set.

The recess detecting section 70 includes an arm 71 made from an elongate body arranged at the bottom portion of the sample setting part 255*a*, and a sensor 72 arranged in the vicinity of one end of the arm 71. The arm 71 is supported in a freely rotating manner at the shaft 73*c* arranged at the bottom of the sample setting part 255*a*. A projection 74 that can enter an accommodation space 255*c* of the sample setting part 255*a* through an opening (not shown) formed in the bottom surface 255*b* of the sample setting part 255*a* is arranged in a standing manner at the other end of the arm 71 (end on the side opposite to the side the sensor 72 is arranged).

The projection 74 enters the recess 80 and is arranged at a position that does not contact with any site of the sample container 101 if the sample container 101 with the recess 80 is set in the sample setting part 255*a*.

The shaft 73 is arranged at a position slightly shifted towards one end side (side on which the projection 74 is arranged in a standing manner) from the center of gravity of the arm 71 so that the projection 74 of the arm 71 is positioned on the upper side than the bottom surface 255*b* of the sample setting part 255*a* in a state other members are not contacting the arm 71 (see FIG. 10A state in which external force is not applied on the arm 71). In other words, the position of the shaft 73 is set so that the arm 71 is biased in the counterclockwise direction in the external force is not applied on the arm 71). In other words, the position of the shaft 73 is set so that the arm 71 is biased in the counterclockwise direction in the example shown in FIG. 10. The arm 71 may be biased using a biasing means such as a spring.

A known sensor based on other principles such as magnetic type or contact type may be appropriately used other than the optical type similar to the sensor 63 for the sensor 72 for detecting the movement of the end of the arm 71.

As shown in FIG. 10A, if the push-up bottom type sample container 101 with the recess 80 is set in the sample setting part 255*a*, the projection 74 of the arm 71 enters the recess 80 and is at the first position of not touching any site of the sample setting part 255*a*. Therefore, the sensor 72 remains turned OFF as the end of the arm 71 on the side the sensor 72 is arranged does not move.

As shown in FIG. 10B, if the sample container 101 without the recess 80 is set in the sample setting part 255*a*, the projection 74 of the arm 71 is pushed against the outer surface of the bottom portion of the sample container 101, so that the arm 71 is rotated in the clockwise direction with the shaft 73 as the center and stopped at a position (second position) the distal end of the projection 74 contacts the outer surface of the bottom portion of the sample container 101 set at a predetermined position in the sample setting part 255*a*. The end of the arm 71 on the side the sensor 72 is arranged thus moves upward and such sensor 72 detects such movement thus becoming sensor ON. The position of the shaft 73 and the weight of the arm 71 are set such that the projection 74 of the arm 71 moves from the first position to the second position only by the weight of the sample container 101.

The CPU 51*a* proceeds the process to step S6-3 when determining that the sample container 101 includes the recess 80 in step S6-2 (Yes), and acquires the lowering amount A from the origin position O corresponding to the sample container 101 with the recess 80 stored in the hard disc 51*d* in step S6-3.

Then, as shown in FIG. 12C, in step S6-4, the CPU 51*a* drives the aspirating tube moving portion to lower the aspirating tube by the lowering amount A acquired in step S6-3 from the origin position O. sample container 101 without the recess 80 stored in the hard disc 51*d* in step S6-5. The lowering amount B is an amount greater than the lowering amount A.

Then, as shown in FIG. 12B, in step S6-6, the CPU 51*a* drives the aspirating tube moving portion to lower the aspirating tube by the lowering amount B acquired in step S6-5 from the origin position O.

When the aspirating tube is lowered to the predetermined lowering position in step S6-4 or step S6-6, the CPU 51*a* aspirates the blood specimen contained in the sample container 101 with the aspirating tube in step S6-7.

After aspiration, the aspirating tube 211 is raised, and the aspirated blood specimen is mixed with the reagent type in the reaction container of the specimen preparing portion 22 to prepare a measurement specimen. The prepared measurement specimen is thereafter transferred to the detecting portion 23 and a predetermined item is measured in the detecting portion 23. The detection result is transmitted to the control unit 51, and the component to be analyzed is analyzed in the control unit 51. The obtained analysis result is displayed on the display unit 52.

After the aspirating tube 211 is raised to the origin position O, the CPU 51a carries out the operation to return the sample container 101 to the original rack 110 (step S7). Specifically, the sample setting part 255a is again moved forward by the drive of the sample container transporting portion 255 and stopped at the sample container setting position 610 by the control of the CPU 51a.

The hand 251 is then lowered from the upper side and stopped at the sample container holding position.

The hand 251 is then closed to hold the sample container 101 of the sample setting part 255a, and then such hand 251 is raised and stopped at a predetermined position.

The sample setting part 255a is taken into the apparatus by the drive of the sample container transporting portion 255 while the hand 251 holding the sample container 101 is being raised. The rack 110, which is moving backward, is then moved forward and stopped at the first retrieving position 43a.

The hand 251 is then lowered and the sample container 101 is inserted to the rack 110, and thereafter, the hand 251 is opened by open driving the open/close part 252 so that the sample container 101 is set in the rack 110.

The hand 251 is then raised. Subsequently, the CPU 51a determines whether or not the sample container accommodating the blood specimen to be analyzed next is present (step S8), and proceeds the process to step S2 to move the rack 110 if there is a next sample container to arrange the sample container 101 accommodating the blood specimen to be analyzed next at the first retrieving position (sample container retrieving position) 43a. Hereinafter, the series of operations described above starting from the lowering of the hand 251 in the open state are repeatedly carried out in a similar manner. If determined that there is no sample container accommodating the blood specimen to be analyzed next in step S8, the CPU 51a terminates the process.

Second Embodiment

A second embodiment of the present invention will now be described with reference to FIG. 2, FIG. 5, FIG. 13 and FIG. 16. The second embodiment is an embodiment particularly useful in an examination room where an operation of a sample of small volume smaller than the normal amount is accommodated in the sample container 101 having the recess 80 and a sample of normal amount is accommodated in the sample container 101 without the recess 80 is carried out. Similar to the first embodiment, the second embodiment changes the lowering amount of the aspirating tube depending on whether or not determination is made that the sample container 101 has the recess 80 in step 9-2 shown in FIG. 14. Furthermore, the diluting magnification and the measurement amount are changed for the sample accommodated in the sample container 101 including the recess 80 and the sample accommodated in the sample container 101 not including the recess 80. The description of the configurations similar to the first embodiment will be omitted.

FIG. 13 is a flowchart showing the flow of the blood specimen processing method using the blood specimen processing apparatus 1. The flow of the blood specimen processing method using the blood specimen processing apparatus 1 will be described using FIG. 13. Step S1 to step S5, step S7, and step S8 are similar to the first embodiment, and hence the description thereof will be omitted. In the second embodiment, the sample processing is a processing including measurement of sample and analysis of measurement data.

After step S5 is finished, the CPU 51a carries out the sample processing, to be described later, in step S9.

<Sample Processing>

Figure 14:
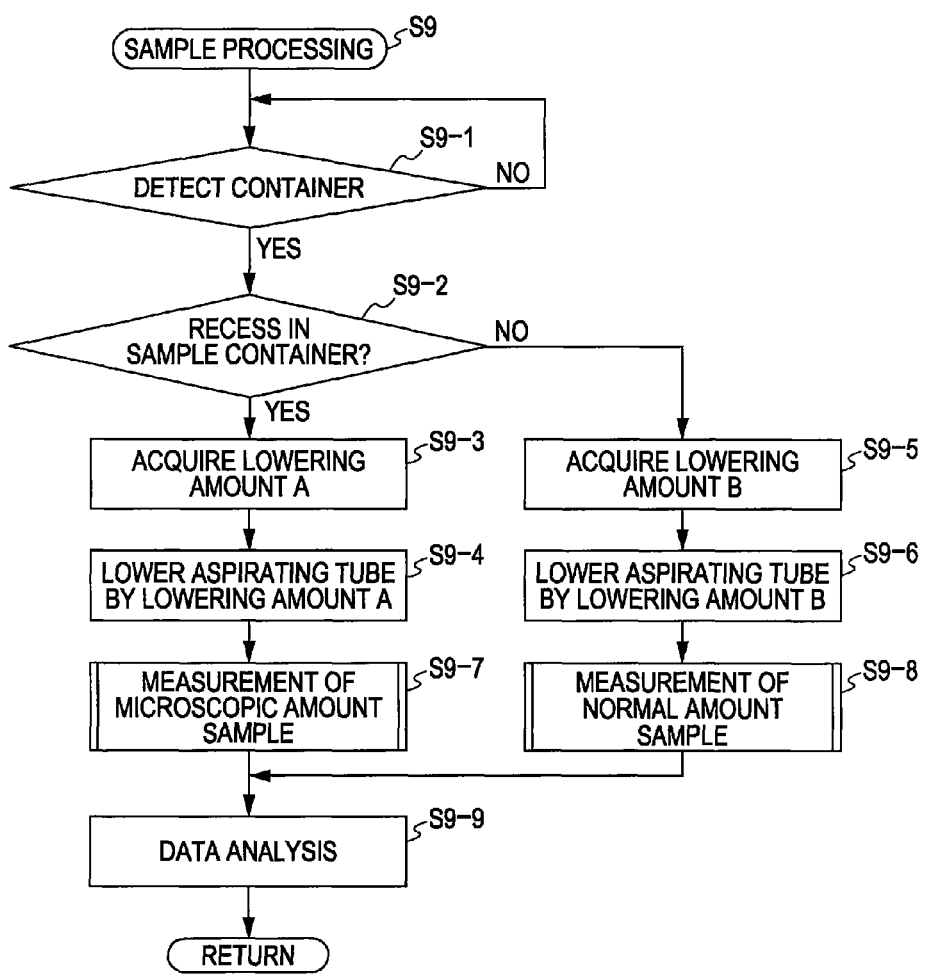
FIG. 14 is a flowchart showing a flow of a sample processing of the blood specimen according to the second embodiment.

The sample processing in step S9 will be described in detail below with reference to FIG. 14. The processes of step S9-1 to step S9-6 are similar to step S6-1 to step S6-6, and hence the description thereof will be omitted.

After step S9-4, the CPU 51a proceeds the process to step S9-7, and executes the measurement of a microscopic amount sample, to be described later. After step S9-6, the CPU 51a proceeds the process to step S9-8, and executes the measurement of the normal amount sample, to be described later.

After the process of step S9-7 or step S9-8, the CPU 51a proceeds the process to step S9-9, executes the analysis of the measurement data, and displays the analysis result on the display unit 52 using tables, distribution diagrams, and the like. After step S9-9, the CPU 51a returns the process to step S7.

[Normal Mode]

Figure 15:
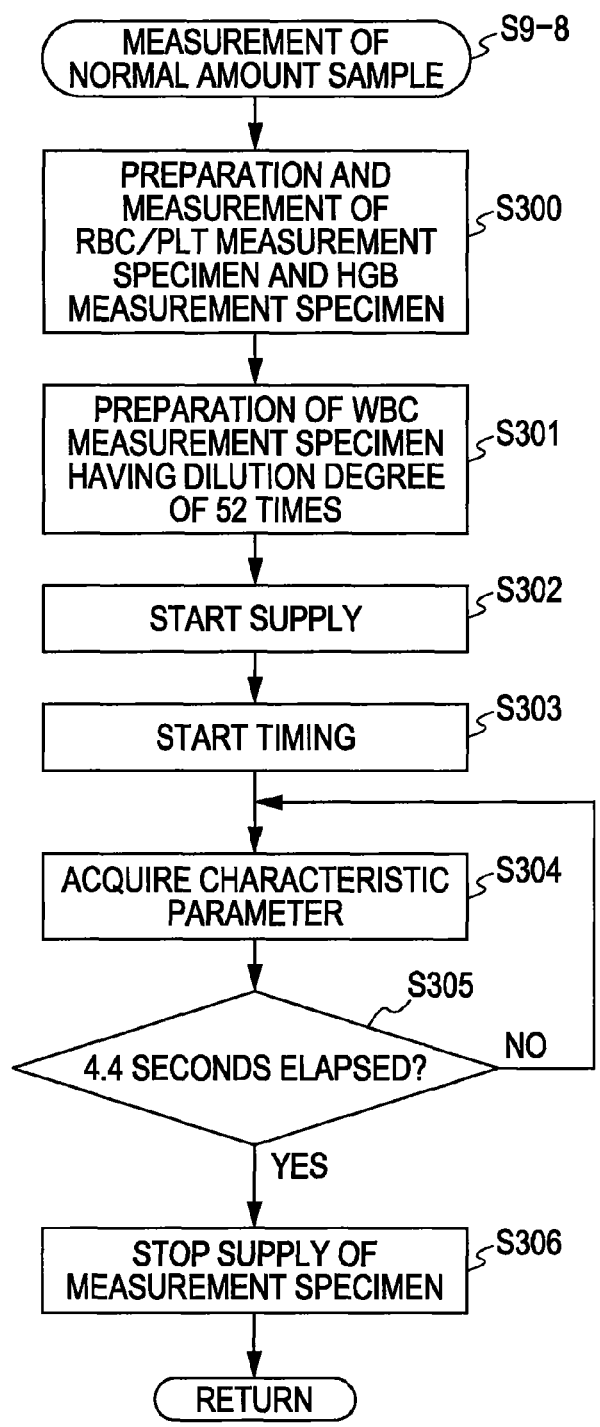
FIG. 15 is a flowchart showing a flow of measurement of a microscopic amount sample.

The normal measurement mode for measuring the sample of normal amount in step S9-8 will now be described with reference to FIG. 15.

First, a predetermined amount of specimen (e.g., 75 µL; numerical value in parentheses hereinafter indicates an example of aspiration amount or usage amount of specimen or reagent) is aspirated by the aspirating tube with a syringe pump.

In step S300, the CPU 51a carries out preparation and measurement of the RBC/PLT measurement specimen and the HGB measurement specimen. Specifically, one part (4 µL) of specimen is mixed with a predetermined amount (2.0 mL) of diluting solution from the aspirating tube to produce a measurement specimen (2.0 mL) diluted to 501 times. One part (RBC/PLT measurement specimen) (1.0 mL) of the produced measurement specimen is introduced to the RBC/PLT detecting portion D1 (electrical resistance type detecting portion), and detection of particles and data collection are carried out for 10.5 seconds. The amount of RBC/PLT measurement specimen to be measured is 10.3 µL. The remaining (1.0 mL) measurement specimen is introduced to the HGB detecting portion D2 and mixed with a predetermined amount (0.5 mL) of hemolytic agent to produce an HGB measurement specimen (1.5 mL) diluted to 751 times. The hemoglobin concentration is measured based on such HGB measurement specimen.

[WBC Measurement]

First, in step S301, the CPU 51a prepares the WBC measurement specimen having a dilution degree of 52 times. Specifically, one part (20 µL) of specimen is mixed with a predetermined amount (1.0 mL) of hemolytic agent and a predetermined amount (20 µL) of stain fluid from the aspirating tube to produce a WBC measurement specimen (1.0 mL) diluted to 52 times.

In step S302, the supply of the produced WBC measurement specimen to the WBC detecting portion D3 is started.

In step S303, the timing of the time from the start of supply of the measurement specimen is started, and in step S304, the characteristic parameters of the measurement specimen are acquired by the WBC detecting portion D3.

In step S305, the CPU 51a determines whether or not 4.4 seconds have elapsed from the start of timing, and returns to step S304 if determined that 4.4 seconds have not elapsed from the start of timing (No) and proceeds to step S306 if determined that 4.4 seconds have elapsed from the start of timing (Yes), and the CPU 51a stops the supply of WBC measurement specimen to the WBC detecting portion D3 in step S306. The amount of WBC measurement specimen measured in this WBC measurement is 39.8 μL.

[Microscopic Amount Mode]

Figure 16:
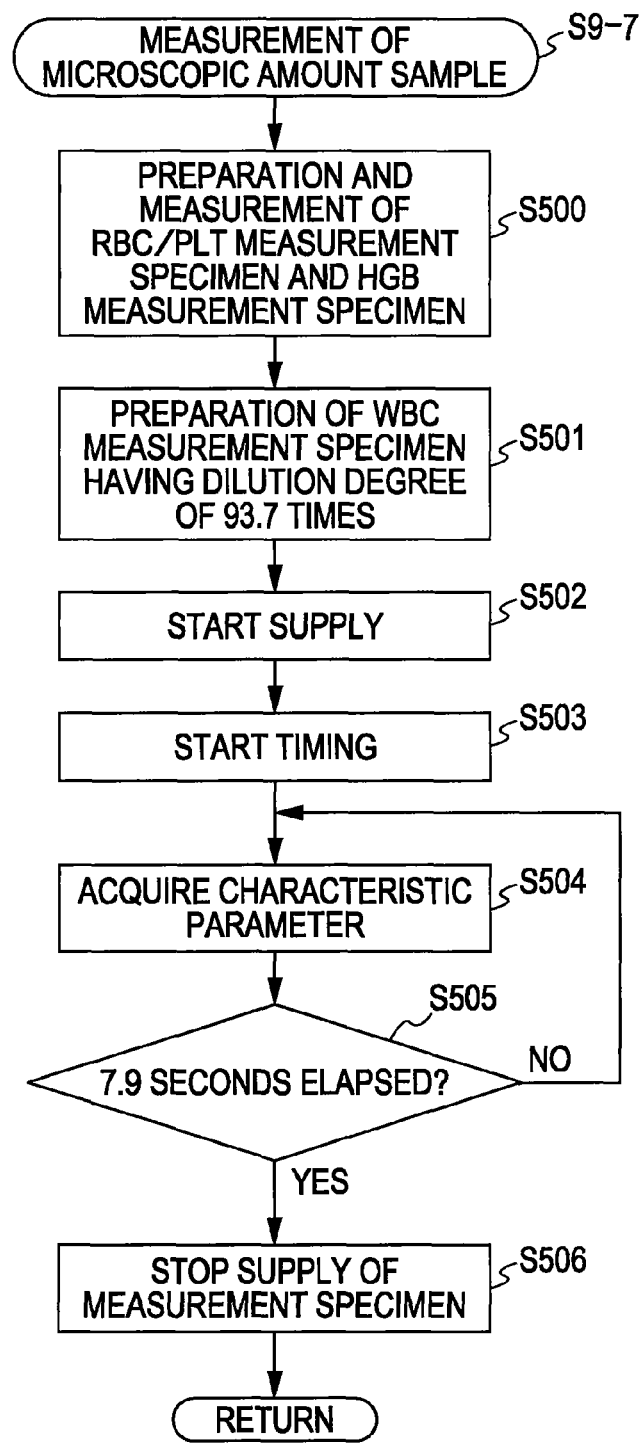
FIG. 16 is a flowchart showing a flow of measurement of a normal amount sample.

The microscopic amount measurement mode for measuring a microscopic amount of sample in step S9-7 will now be described with reference to FIG. 16.

First, a predetermined amount of specimen (48 μL) is aspirated by the aspirating tube with a syringe pump.

In step S500, the CPU 51a carries out preparation and measurement of the RBC/PLT measurement specimen and the HGB measurement specimen. Specifically, one part (4 μL) of specimen is mixed with a predetermined amount (2.0 mL) of diluting solution from the aspirating tube to produce a measurement specimen (2.0 mL) diluted to 501 times. One part (RBC/PLT measurement specimen) (1.0 mL) of the produced measurement specimen is introduced to the RBC/PLT detecting portion D1 (electrical resistance type detecting portion), and detection of particles and data collection are carried out for 10.5 seconds. The amount of RBC/PLT measurement specimen to be measured is 10.3 μL. The remaining (1.0 mL) measurement specimen is introduced to the HGB detecting portion D2 and mixed with a predetermined amount (0.5 mL) of hemolytic agent to produce an HGB measurement specimen (1.5 mL) diluted to 751 times. The hemoglobin concentration is measured based on such HGB measurement specimen.

[WBC Measurement]

First, in step S501, the CPU 51a prepares the WBC measurement specimen having a dilution degree of 93.7 times. Specifically, one part (11 μL) of specimen is mixed with a predetermined amount (1.0 mL) of hemolytic agent and a predetermined amount (20 μL) of stain fluid from the aspirating tube to produce a WBC measurement specimen (1.0 mL) diluted to 93.7 times.

In step S502, the supply of the produced WBC measurement specimen to the WBC detecting portion D3 is started.

In step S503, the timing of the time from the start of supply of the measurement specimen is started, and in step S504, the characteristic parameters of the measurement specimen are acquired by the WBC detecting portion D3.

In step S505, the CPU 51a determines whether or not 7.9 seconds have elapsed from the start of timing, and returns to step S504 if determined that 7.9 seconds have not elapsed from the start of timing (No) and proceeds to step S506 if determined that 7.9 seconds have elapsed from the start of timing (Yes), and the CPU 51a stops the supply of WBC measurement specimen to the WBC detecting portion D3 in step S506. The amount of WBC measurement specimen measured in this WBC measurement is 71.4 μL.

The blood specimen processing apparatus 1 is configured such that the supply speed of the measurement specimen supplied to the detecting portion in the case of the microscopic amount measurement mode is the same as the supply speed of the measurement specimen supplied to the detecting portion in the case of the normal measurement mode.

As described above, in the blood specimen processing apparatus 1 according to the second embodiment, the amount (48 μL) of specimen to be aspirated becomes less if the microscopic amount measurement mode is selected compared to the normal measurement mode (75 μL). In the case of the WBC measurement, the dilution degree (93.7 times) of the measurement specimen becomes high compared to the normal measurement mode (52 times), but the measurement accuracy can be raised even if the dilution degree is high since the measurement specimen of an amount (71.4 μL) greater than the measurement amount (39.8 μL) in the normal measurement mode is being measured by measuring the measurement specimen for a time (7.9 seconds) longer than the measurement time (4.4 seconds) in the normal measurement mode.

In the second embodiment, if the microscopic amount measurement mode is selected, for instance, in the case of the WBC measurement, the measurement specimen is measured for a time longer than in the normal measurement mode, and hence a greater amount of measurement specimens than the normal measurement mode can be measured if the speed of the measurement specimen flowing through the detecting portion in the case of the microscopic amount measurement mode and the speed of the measurement specimen flowing through the detecting portion in the case of the normal measurement mode are the same. Thus, the supply speed of the measurement specimen to the detecting portion becomes the same in either measurement mode, and the specimen can be measured under the same condition.

Third Embodiment

A third embodiment of the present invention will now be described with reference to FIG. 2, and FIG. 17 to FIG. 21. The third embodiment is an embodiment particularly useful in an examination room where an operation in which blood of the child from which only the sample of small volume smaller than the normal amount can be often collected is contained in the sample container 101 including the recess 80 and a blood of the adult from which a normal amount of sample can be collected is contained in the sample container 101 not including the recess 80 is carried out. Similar to the first embodiment, the third embodiment changes the lowering amount of the aspirating tube depending on whether or not determination is made that the sample container 101 has the recess 80 in step 10-2 shown in FIG. 20. Furthermore, the analyzing condition of the measurement data is changed for the sample accommodated in the sample container 101 including the recess 80 and the sample accommodated in the sample container 101 not including the recess 80. The description of the configurations similar to the first embodiment will be omitted.

Figure 17:
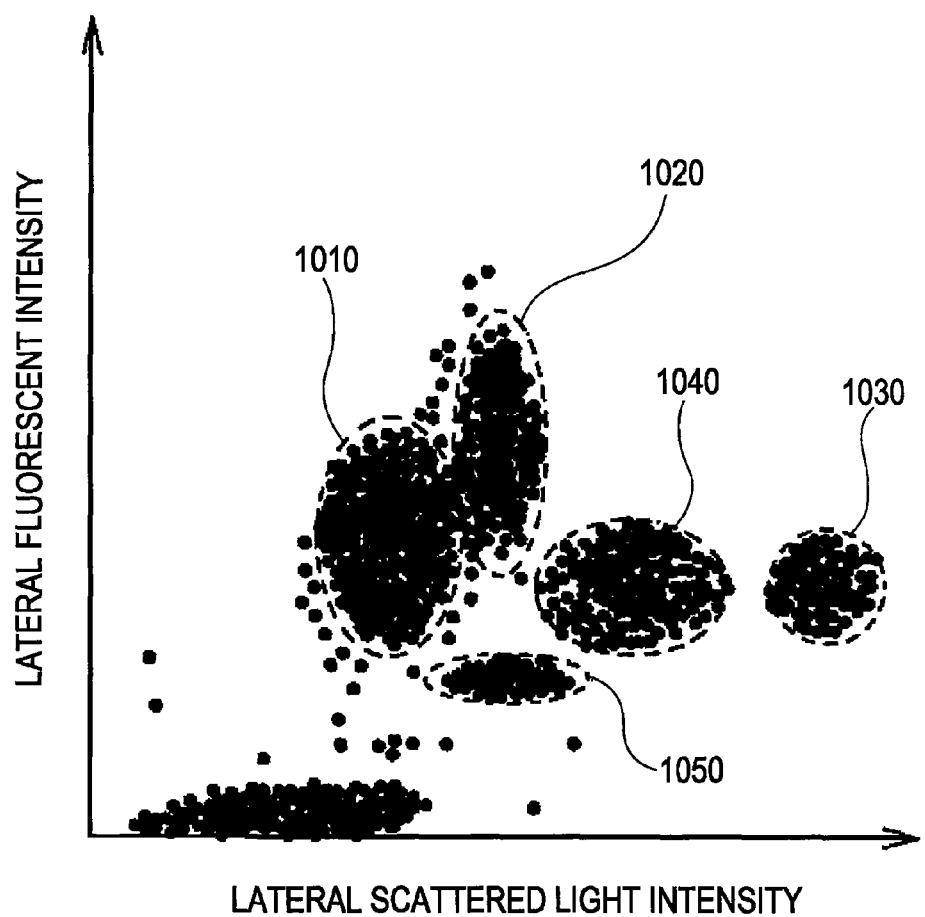
FIG. 17 is an illustrative view of a scattergram at the time of the white blood cell classification measurement (DIFF measurement)

When the blood of the adult is measured, and the white blood cells contained in the blood are classified to lymphocytes, the monocytes, the neutrophils, the basocytes, the acidocytes (white blood cell classification measurement (referred to as DIFF measurement)) in the blood specimen processing apparatus 1 according to the third embodiment, a scattergram shown in FIG. 17 is created and displayed on the display unit 52. FIG. 17 is an illustrative view of a scattergram at the time of the white blood cell classification measurement (DIFF measurement). In FIG. 17, the vertical axis indicates the lateral fluorescent light intensity and the horizontal axis indicates the lateral scattered light intensity. The method of classifying the white blood cells used in the blood specimen processing apparatus 1 according to the third embodiment will be described below.

As shown in FIG. 17, in the blood specimen processing apparatus 1 according to the third embodiment, a lymphocyte distribution region 1010 in which the lymphocytes are assumed to be distributed, a monocyte distribution region 1020 in which the monocytes are assumed to be distributed, a acidocyte distribution region 1030 in which acidocytes are assumed to be distributed, a neutrophil distribution region 1040 in which neutrophils are assumed to be distributed, and a basocyte distribution region 1050 in which basocytes are assumed to be distributed are defined in advance based on the past statistical values of an adult blood. The integer column information is sampled based on the measurement data on the same coordinate axis, and thereafter, the attribution degree of the blood cells to each distribution region of the lymphocyte distribution region 1010, the monocyte distribution region 1020, the acidocyte distribution region 1030, the neutrophil distribution region 1040, and the basocyte distribution region 1050 is calculated, and each blood cell is classified to the blood cell of a specific type according to the calculated attribution degree. The number of lymphocytes, monocytes, and the like can be obtained by counting the classified blood cells. The method of classifying the white blood cells described above is described in detail in U.S. Pat. No. 5,555,196. The computer program for executing the method of classifying the white blood cells described above and the data used in the execution of the computer program are stored in advance in the hard disc 51d.

Figure 18:
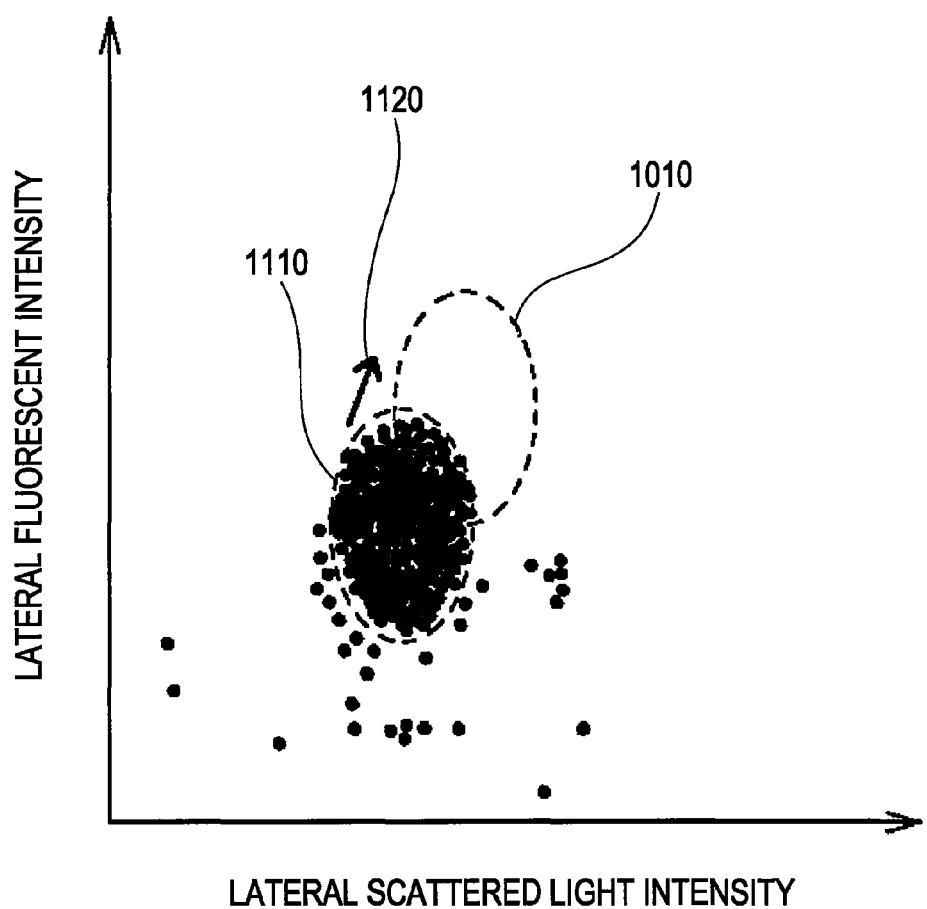
FIG. 18 is an illustrative view of a relationship of the lymphocyte distribution region of the scattergram created at the time of the DIFF measurement and the sampling value.

The blood cells contained in the blood of the child has a lower degree of being stained by the stain fluid compared to the blood cells contained in the blood of the adult. Thus, with respect to the measurement data obtained by measuring the blood of the child, the sampling values tend to be distributed slightly on the lower side of each region to be originally distributed shown in FIG. 17. FIG. 18 is an illustrative view of a relationship of the lymphocyte distribution region 101 of the scattergram created at the time of the DIFF measurement and the sampling value.

As shown in FIG. 18, the sampling values are assumed to be aggregated around the lymphocyte distribution region 1010 if the measurement data is the blood of the adult. However, if the measurement data is the blood of the child and not the blood of the adult, the fluorescence intensity and the scattered light intensity are both measured low since the staining degree by the stain fluid is lower for the blood of the child than for the blood of the adult. Therefore, the sampling values are aggregated near the region 1110 on the lower side of the lymphocyte distribution region 1010.

If the distribution tendency is shifted as a whole to the lower side of the assumed region from the scattergram, determination can be made that the measurement data is data targeted on the blood of the child, and it can be recognized that the region 1110 where the sampling values are aggregated needs to be shifted in the direction of the arrow 1120 to enhance the accuracy of the classification process. A means for shifting up the measurement data targeted on the blood of the child to accurately execute the classification process using the blood cell classification method same as when the white blood cells are classified on the basis of the blood of the adult even if the measurement data is the data targeted on the blood of the child will be described below.

Figure 19:
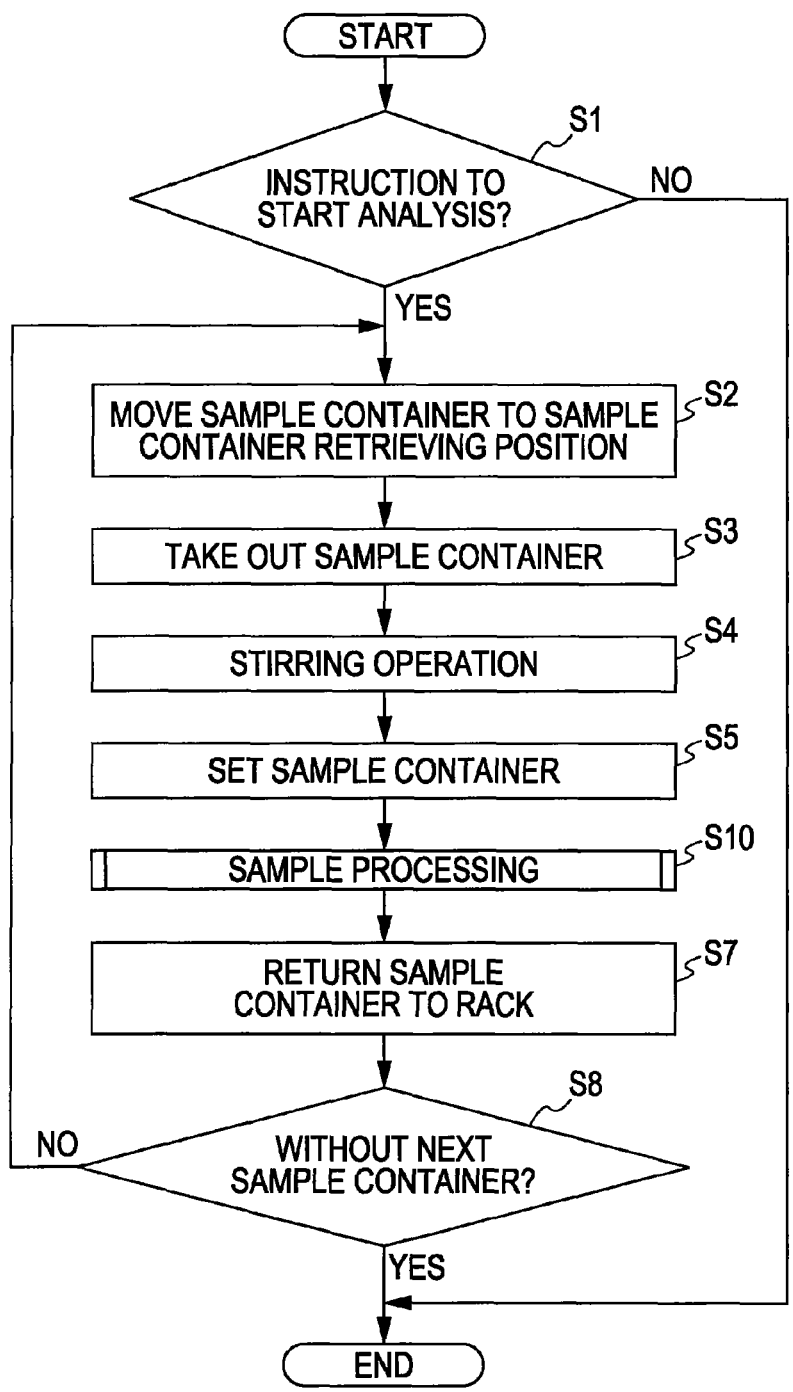
FIG. 19 is a flowchart showing the flow of processes of the blood specimen processing method according to a third embodiment.

FIG. 19 is a flowchart showing the flow of the blood specimen processing method using the blood specimen processing apparatus 1. The flow of the blood specimen processing method using the blood specimen processing apparatus 1 will be described using FIG. 19. Step S1 to step S5, step S7, and step S8 are similar to the first embodiment, and hence the description thereof will be omitted. In the third embodiment, the sample processing is a processing including measurement of sample and analysis of measurement data.

Figure 20:
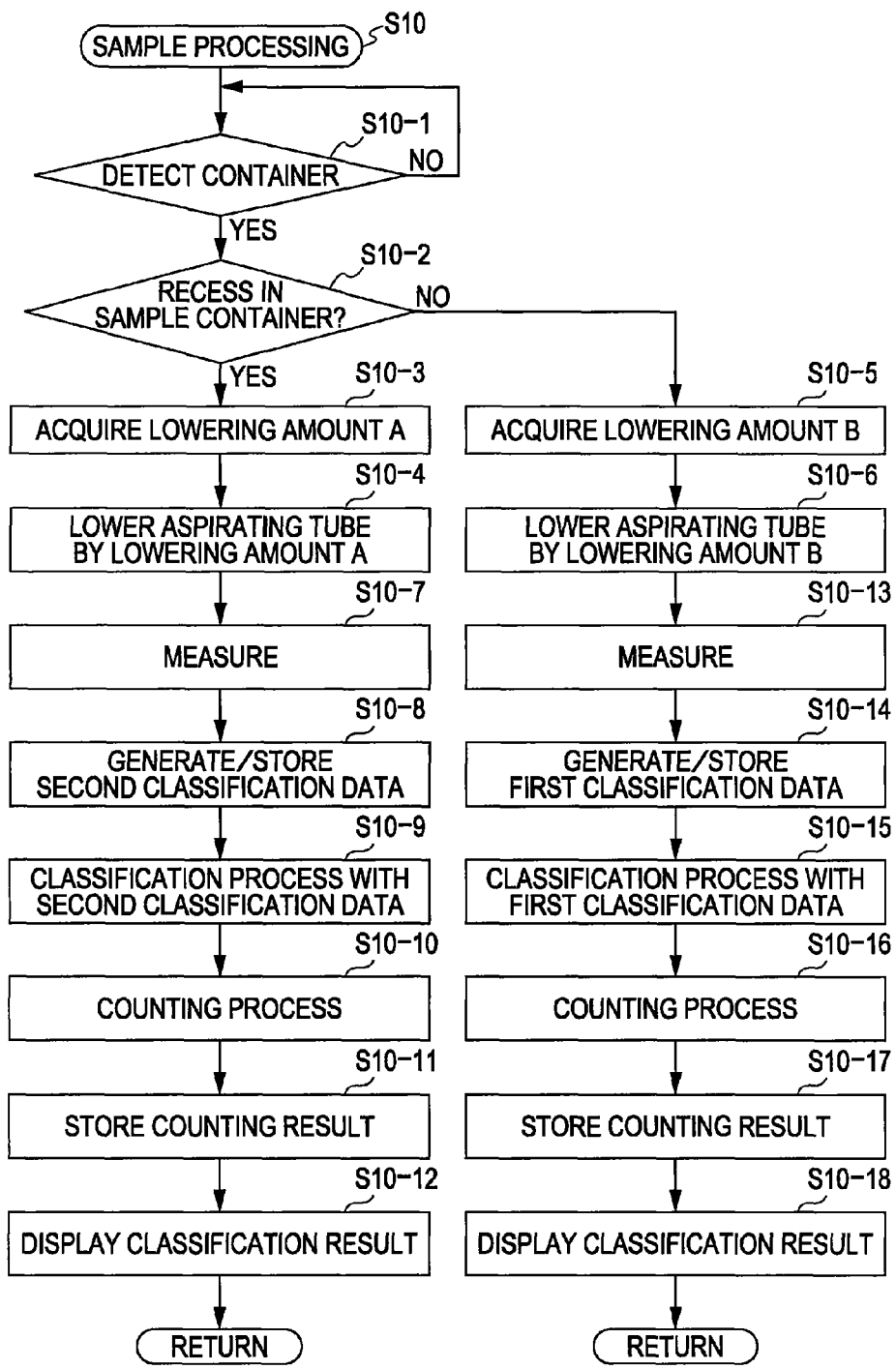
FIG. 20 is a flowchart showing the flow of the sample processing of the blood specimen according to the third embodiment.

After step S5 is finished, the CPU 51a carries out the sample processing, to be described later, in step S10.
<Sample Processing>
The sample processing in step S10 will be described in detail below with reference to FIG. 20. The processes of step S10-1 to step S10-6 are similar to step S6-1 to step S6-6, and hence the description thereof will be omitted.

After step S10-6, the CPU 51a controls the specimen preparing portion 22 (32) to prepare the measurement specimen, and then carries out the measurement of the measurement specimen (step S10-13). Specifically, the CPU 51a executes the detection for DIFF measurement by the optical detecting portion D3, converts the electrical signals corresponding to the light receiving intensities of the lateral scattered light and the lateral fluorescence to a digital signal of 12 bits, performs a predetermined process on the digital signal, and acquires the integer column information of 12 bits as measurement data (step S10-13).

Following step S10-13, the CPU 51a generates a first classification data or integer column information of 8 bits based on the acquired measurement data (e.g., integer column information of 12 bits), and stores the same in the measurement result DB 54d (step S10-14). Specifically, the CPU 51a reduces the acquired integer column information of 12 bits to the integer column information of 8 bits as is to generate the first classification data.

Similar to step S10-13, following step S10-4, the CPU 51a controls the specimen preparing portion 22 (32) to prepare the measurement specimen, and then carries out the measurement of the measurement specimen (step S10-7).

Following step S10-7, the CPU 51a 1.2 times the acquired integer column information of 12 bits and reduces the integer portion to the integer column information of eight bits to generate second classification data, and stores the same in the measurement result DB 54d (step S10-8). The data value of the second classification data for the blood of the child is thus generated greater than the data value of the first classification data for the blood of the adult. Since the staining degree by staining of the blood cells is lower for the blood of the child with respect to the blood of the adult and the blood of the child, the integer column information acquired for the blood of the child needs to be slightly pulled up to classify the blood cells in the blood using the blood cell classification method same as for the blood of the adult.

Figure 21:
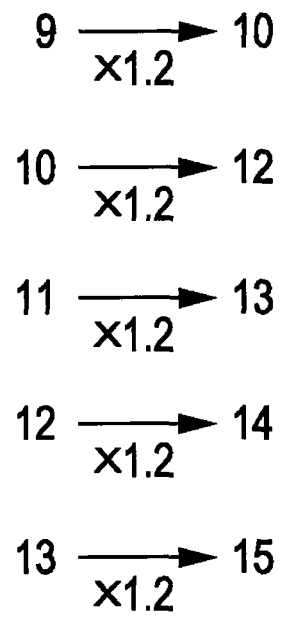

The proportion of maintaining continuity of the integer value can be enhanced compared to when simply making the first classification data for the blood of the adult to 1.2 times to generate the second classification data by making the integer column information of 12 bits to 1.2 times and then reducing to the integer column information of 8 bits to generate the second classification data for the blood of the child. FIG. 21 is an illustrative view of the calculation processing result of the measurement data. As shown in FIG. 21, when the measurement data is the successive integer values of 9 to 13, "11" will be missing in the integer values obtained by simply making such integer values to 1.2 times and successive integer values will not be obtained. The accurate counting result may not be obtained when classifying the particles to plural types.

In the third embodiment, the measurement data is acquired as the integer column information having the number of bits (12 bits) greater than the number of bits (8 bits) used in the classification process and then made to 1.2 times, the integer portion thereof is reduced to the integer column information of 8 bits to generate the second classification data for the blood of the child, and the classification process is executed using the generated second classification data. The proportion of maintaining continuity of the integer values is thus enhanced. In other words, the integer column information of 12 bits is made to 1/16 times when generating the first classification data for the blood of the adult and the integer column information of 12 bits is made to 1.2/16 times when generating the second classification data for the blood of the child, so that the range of measurement data that may take the same integer value when made to 1.2/16 times becomes greater and the error is less likely to stand out.

Consider a case where the frequency of each element (X1, X2) (X1, X2=0, 1, 2, . . . ) in the two-dimensional distribution data Dn having N×N (N is a natural number) elements is F(X1, X2), and the two-dimensional distribution data Dn is reduced to the two-dimensional distribution data Dm having M×M (M is a natural number) elements. Here, M<N.

Each element (X1, X2) in the two-dimensional distribution data Dn having N×N elements corresponds to the element (U1, U2) (U1, U2=0, 1, 2, . . . M) shown in equation (1) in the distribution data Dm. In equation (1), Int(x) is the function representing the integer portion of the argument x. This corresponds to the process of reducing the measurement data of 12 bits to 8 bits.

$$(U1, U2) = (\text{Int}(X1 \times M/N), \text{Int}(X2 \times M/N)) \quad (1)$$

When converting the two-dimensional distribution data DL having the partial region of L×L elements in the two-dimensional distribution data Dm to the two-dimensional distribution data having M×M elements (L<M<N), each element (X1, X2) (X1, X2=0, 1, 2, . . . , N×L/M) in the distribution data Dn corresponds to (V1, V2) (V1, V2=0, 1, 2, . . . , M) in the distribution data Dml, as shown in equation (2). This corresponds to the process of shifting up the data of 8 bits substantially to the upper side.

$$(V1, V2) = (\text{Int}(X1 \times M2/(N \times L)), \text{Int}(X2 \times M2/(N \times L))) \quad (2)$$

In other words, for the process similar to the process of equation (1), the two-dimensional distribution data DL having the partial region of L×L elements is first converted (enlarged) to the two-dimensional distribution data having N×N elements, and then converted to the two-dimensional data having M×M elements so that the frequency of each element of the distribution data Dml is calculated and a smooth distribution data can be obtained.

The description will return to FIG. 20. Following step S10-8, the CPU 51a reads out the second classification data from the measurement data DB 54d, and executes the classification process based on the read second classification data (step S10-9).

The CPU 51a then counts the number of blood cells of the classified lymphocytes, monocytes, acidocytes, neutrophils, and basocytes (step S10-10). The CPU 51a stores the counting result in the measurement DB 54d (step S10-11), displays the classification result on the display unit 52 (step S10-12), and returns the process to step S7 of FIG. 19.

Following step S10-14, the CPU 51a reads out the first classification data from the measurement data DB 54d, and executes the classification process based on the read first classification data (step S10-15).

The CPU 51a then counts the number of blood cells of the classified lymphocytes, monocytes, acidocytes, neutrophils, and basocytes (step S10-16). The CPU 51a stores the counting result in the measurement DB 54d (step S10-17), displays the classification result on the display unit 52 (step S10-18), and returns the process to step S7 of FIG. 19.

Here, "child" may also refer to a newborn, an infant, or a toddler. The term "child" does not only refer to subjects of a predetermined age or under, and the subject going to pediatrics or obstetrician may be a "child", or a child before enrolling in elementary school may be a "child". The manufacturing company that manufactures the living body specimen analyzer may set the range of "child".

In the third embodiment, a configuration of accurately carrying out the analyzing process on the blood of the child and also on the blood of the adult by changing the analyzing condition of the measurement data for when measuring the blood of the child and for when measuring the blood of the adult has been described, but the present invention is not limited thereto.

The classification process can be accurately carried out on the blood of the child and also on the blood of the adult by reducing the sample dispensing amount or increasing the dispensing amount of the stain reagent in the case of the small volume sample container (sample container in which recess 80 is detected) than in the case of the normal sample container (sample container in which recess 80 is not detected) to raise the mixing ratio of the stain reagent with respect to the sample thus promoting the stain reaction. The stain reaction can be promoted by making the reaction time for the sample and the stain reagent longer instead of raising the mixing ratio of the stain reagent respect to the sample. Therefore, the specimen preparation result of the same extent as the normal sample can be obtained for the sample that is less likely to be stained compared to the normal sample by changing the specimen preparation condition in the specimen preparing portion, and subsequent processes such as specimen measurement and analysis can be satisfactorily carried out. Such specimen preparation condition is stored in the hard disc, where the necessary information is read out and the specimen preparation is executed based on such information with the detection result of the recess.

The specimen measurement condition may be controlled in the specimen measurement section instead of changing the analysis condition of the measurement data for when measuring the blood of the child and for when measuring the blood of the adult.

Specifically, the fluorescence emitted from the specimen is detected at high sensitivity by processes such as increasing the irradiation light intensity in the optical detecting portion D3 or enhancing the detection sensitivity of the fluorescence in the case of the small volume sample container than in the case of the normal sample container, so that the specimen measurement result of the same extent as the normal sample can be obtained even for the child sample in which signal detection is difficult compared to the normal sample, and the subsequent processes such as data analysis can be satisfactorily carried out.

[Other Variants]

The present inventions may be appropriately design changed without being limited to the embodiments described above.

For instance, in the embodiment described above, the presence or absence of the recess 80 of the sample container 101 is detected by the recess detecting section 70 using the projection 74 that contacts the sample container when the sample container does not have the recess, but other than such contact type detection, the presence or absence of the recess 80 may be detected using other principles such as optical or magnetic. The recess 80 of the sample container 101 may be detected using the ultrasound wave.

Figure 11:
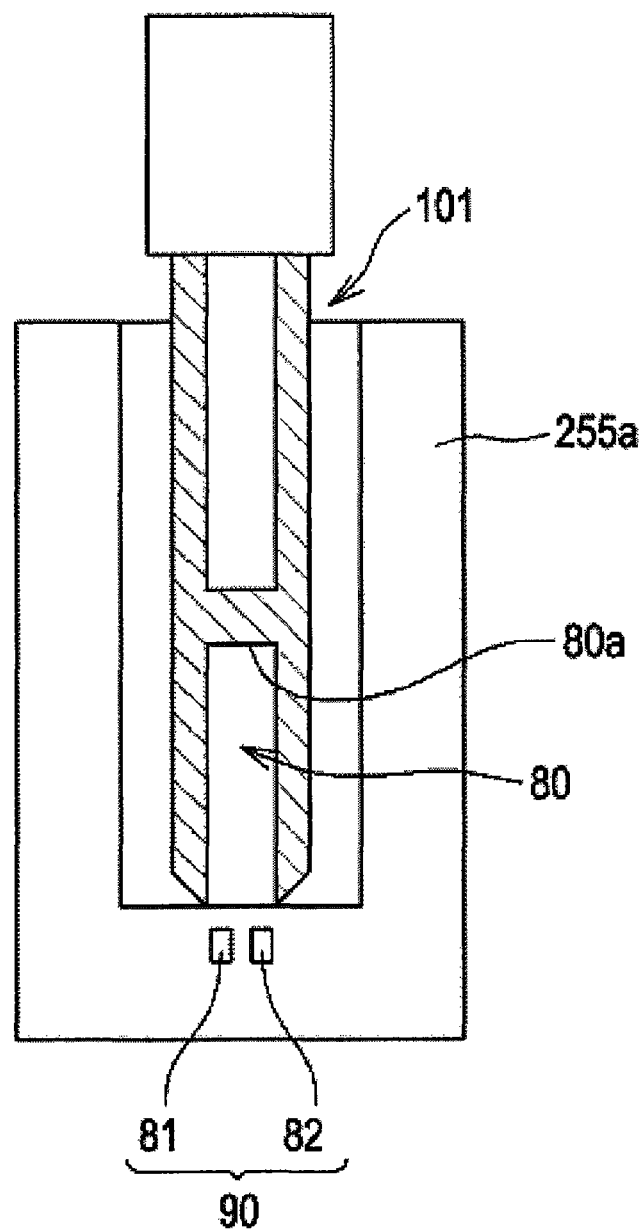
FIG. 11 is an explanatory view of an optical recess detecting section.

FIG. 11 is a view describing the principle of optically detecting the presence or absence of the recess 80 or the principle other than detecting the presence or absence of the recess 80 by the recess detecting section 70. A recess detecting section 90 is arranged in the sample setting part 255a, and is configured by a light emitting part 81 that emits light towards a top surface 80a of the recess 80 of the sample container 101 set in the sample setting part 255a, and a light receiving part 82 that receives the light mainly reflected by the top surface 80a. If the sample container 101 without the recess 80 is set in the sample setting part 255a, the light from the light emitting part 81 hits the outer surface of the bottom portion of the sample container 101 and barely reaches the light receiving part 82. In other words, the amount of light reaching the light receiving part 82 is less than the amount of light reflected mainly by the top surface 80a in the sample container 101 with the recess 80 and reaching the light receiving part 82, so that the presence or absence of the recess 80 can be detected using such difference.

In the embodiment described above, the projection 74 is arranged at the end of the rotatable arm 71, and the presence or absence of the recess 80 of the sample container 101 is detected using the contact of the projection 74 and the sample container, but the arm 71 may be omitted, and the recess 80 of the sample container 101 may be detected by the projection arranged in a recessed area formed at the bottom portion of the sample setting part 255a. In this case, the projection is configured to enter the accommodation space 255c of the sample setting part 255a by the biasing means such as a spring, and move backward into the recessed area by the contact with the outer surface of the bottom portion of the sample container 101 without the recess 80. The presence or absence of the recess 80 of the sample container 101 can be detected as the back end (end on the side opposite to the distal end that contacts the outer surface of the bottom portion of the sample container 101) of the projection pushes the microswitch when moved backward into the recessed area.

In the embodiment described above, the presence or absence of the recess 80 of the sample container 101 is indirectly detected through the projection 74 of the arm 71, but the presence or absence of the recess 80 of the sample container 101 may be directly detected by the pressure sensor or the load sensor arranged at the bottom surface of the sample container 101.

Furthermore, in the embodiment described above, the amount the aspirating tube 211 lowers from the origin position O is stored in the hard disc 51d in correspondence with the type of sample container, but the distance from the origin position O to the bottom surface on the inner side of the sample container may be stored in the hard disc 51d in correspondence with the type of sample container and the amount the aspirating tube 211 lowers may be calculated from the stored distance.

In the embodiment described above, the aspirating tube is moved to aspirate the sample in the sample container, but the sample container may be moved towards the aspirating tube by the drive mechanism and the distal end of the aspirating tube may be positioned at a predetermined position in the sample container. In this case, the drive mechanism and the aspirating tube are controlled by the control unit such that the aspirating tube is positioned at a first depth in the sample container to aspirate the sample when aspirating the sample from the sample container in which the recess is not detected by the recess detecting section, and the aspirating tube is positioned at a second depth shallower than the first depth to aspirate the sample when aspirating the sample from the sample container in which the recess is detected by the recess detecting section. The first depth is set at a position on the upper side by a predetermined distance from the inner side of the bottom portion of the container so that the aspirating tube inserted into the sample container without the recess does not get damaged by contacting the inner side of the bottom portion of the container and so that the sample can be aspirated. The second depth is set at a position on the upper side by a predetermined distance from the inner side of the bottom portion of the container so that the aspirating tube inserted into the sample container with the recess does not get damaged by contacting the inner side of the bottom portion of the container and so that the sample can be aspirated. The second depth is set to be shallower than the first depth.

In the embodiment described above, the aspirating tube is lowered based on the aspirating position information (lowering position) stored in advance in the hard disc 51d, but an accepting portion for accepting change of the aspirating position information stored in the storage unit may be arranged to change the aspirating position information. The input device 53 may be used for the accepting portion. In this case, the sample containers having different bottom portion position may be used even if they are the same push-up bottom type sample containers.

In the embodiment described above, the blood specimen is used for the sample, the blood cell counting device or one of the blood specimen processing apparatus is used for the sample processing apparatus, and the blood cells in such blood specimen is counted, but the present invention is not limited thereto. The present invention may be applied to the sample processing apparatus such as the blood specimen processing apparatus and the urine analyzer as the sample processing apparatus. Application can also be made to the blood cell counting device, the immune analyzer, the blood coagulation measurement device, the biochemical analyzer, the blood smear creating device, and the like as the blood specimen processing apparatus. Application can also be made on a device for processing body fluid other than blood such as cerebral spinal fluid, pleural effusion, peritoneal fluid, pericardial fluid, joint fluid, or the like other than the blood specimen.

What is claimed is:

1. A sample processing apparatus for processing a sample accommodated in a sample container comprising:
    a first type of sample container that includes a recess formed on an outer side of the bottom surface;
    a second type of sample container that does not include a recess formed on an outer side of the bottom surface;
    a holder on which the first type of sample container and the second type of sample container is to be set;
    a sample processing unit configured to process a sample accommodated in a sample container set in the holder, wherein the sample processing unit includes a sample aspirating portion configured to aspirate the sample accommodated in the first type of sample container and the second type of sample container, the sample aspirating portion including an aspirating tube for aspirating the sample accommodated in the sample container and an actuator for moving the aspirating tube in an up and down direction;
    a recess detector configured to detect the recess of the sample container set in the holder; and
    a controller configured to control the sample processing unit to process the sample under a first aspirating condition for aspirating the sample by the aspirating tube lowered to a first height if the recess is not detected by the recess detector, and to process the sample under a second aspirating condition for aspirating the sample by the aspirating tube lowered to a second height higher than the first height if the recess is detected by the recess detector.

2. The sample processing apparatus according to claim 1, wherein the recess detector includes an arm that contacts an outer surface of the bottom surface of the sample container when the sample container held in the holder does not include the recess on the outer side of the bottom surface.

3. The sample processing apparatus according to claim 2, wherein the arm is configured to be movable between a first position positioned when the sample container held in the holder includes the recess on the outer side of the bottom surface, and a second position positioned when the sample container held in the holder does not include the recess on the outer side of the bottom surface.

4. The sample processing apparatus according to claim 3, wherein at least one part of the arm is inserted to the recess of the sample container at the first position.

5. The sample processing apparatus according to claim 2, further comprising: a container detecting part for detecting presence or absence of the sample container in the holder, wherein the controller is configured to detect whether or not there is the recess on the outer side of the bottom surface of the sample container with the recess detector when the presence of the sample container in the holder is detected by the container detecting part.

6. The sample processing apparatus according to claim 3, wherein the arm is configured to be positioned at the first position when the sample container is not held in the holder.

7. The sample processing apparatus according to claim 3, wherein the arm is movable from the first position to the second position with the weight of only the sample container.

8. The sample processing apparatus according to claim 1, wherein the sample processing unit includes a specimen preparing portion for preparing a measurement specimen by mixing the sample accommodated in the sample container and a reagent, and
the controller controls the sample processing unit to process the sample under a condition for diluting the sample at a first magnification by the specimen preparing portion if the recess is not detected by the recess detector, and to process the sample under a condition for diluting the sample at a second magnification greater than the first magnification by the specimen preparing portion if the recess is detected by the recess detector.

9. The sample processing apparatus according to claim 8, wherein the sample processing unit includes a specimen detector for measuring the measurement specimen prepared by the specimen preparing portion, and
the controller controls the sample processing unit to process the sample under a condition for measuring a first measurement amount of the measurement specimen by the specimen detector if the recess is not detected by the recess detector, and to process the sample under a condition for measuring a second measurement amount greater than the first measurement amount of the measurement specimen by the specimen detector if the recess is detected by the recess detector.

10. The sample processing apparatus according to claim 1, wherein the sample processing unit includes a specimen detector for measuring the measurement specimen prepared by mixing a sample and a reagent, and
the controller controls the sample processing unit to process the sample under a condition for measuring a first measurement amount of the measurement specimen by the specimen detector if the recess is not detected by the recess detector, and to process the sample under a condition for measuring a second measurement amount greater than the first measurement amount of the measurement specimen by the specimen detector if the recess is detected by the recess detector.

11. The sample processing apparatus according to claim 1, wherein the sample processing unit includes a specimen preparing portion for preparing a measurement specimen by mixing the sample accommodated in the sample container and a reagent, and a specimen detector for measuring the measurement specimen prepared by the specimen preparing portion, and
the controller controls the sample processing unit to process the sample under a condition for detecting the measurement specimen at a first detection sensitivity by the specimen detector if the recess is not detected by the recess detector, and to process the sample under a condition for detecting the measurement specimen at a second detection sensitivity higher than the first detection sensitivity by the specimen detector if the recess is detected by the recess detector.

12. The sample processing apparatus according to claim 1, wherein the sample processing unit includes a specimen preparing portion for preparing a measurement specimen by mixing the sample accommodated in the sample container and a reagent, a specimen detector for measuring the measurement specimen prepared by the specimen preparing portion, and an analyzing portion for analyzing measurement data obtained by being measured by the specimen detector, and
the controller controls the sample processing unit to process the sample under a condition for analyzing the measurement data under a first analyzing condition by the analyzing portion if the recess is not detected by the recess detector, and to process the sample under a condition for analyzing the measurement data under a second analyzing condition different from the first analyzing condition by the analyzing portion if the recess is detected by the recess detector.

13. The sample processing apparatus according to claim 1, wherein the recess detector is a light detector for optically detecting the recess of the sample container held in the holder.

14. The sample processing apparatus according to claim 1, wherein the controller controls the sample processing unit to process the sample under a condition for aspirating the sample of a first amount by the sample aspirating portion if the recess is not detected by the recess detector, and to process the sample under a condition for aspirating the sample of a second amount less than the first amount by the sample aspirating portion if the recess is detected by the recess detector.

15. The sample processing apparatus according to claim 1, wherein the sample processing unit includes a specimen preparing portion for preparing a measurement specimen by mixing the sample accommodated in the sample container and a reagent, and
the controller controls the sample processing unit to process the sample under a condition for mixing the sample and the reagent at a first proportion by the specimen preparing portion if the recess is not detected by the recess detector, and to process the sample under a condition for mixing the sample and the reagent at a second proportion, in which the ratio of the reagent is greater than the first proportion, by the specimen preparing portion if the recess is detected by the recess detector.

16. The sample processing apparatus according to claim 1, wherein the sample processing unit includes a specimen preparing portion for preparing a measurement specimen by mixing the sample accommodated in the sample container and a reagent, and
the controller controls the sample processing unit to process the sample under a condition for reacting the sample and the reagent for a first time by the specimen preparing portion if the recess is not detected by the recess detector, and to process the sample under a condition for mixing the sample and the reagent for a second time longer than the first time by the specimen preparing portion if the recess is detected by the recess detector.

* * * * *